US007456263B2

(12) United States Patent
Sherman et al.

(10) Patent No.: US 7,456,263 B2
(45) Date of Patent: Nov. 25, 2008

(54) P53 BINDING T CELL RECEPTOR MOLECULES

(75) Inventors: Linda A. Sherman, LaJolla, CA (US); Kimberlyn F. Card, Pembroke Pines, FL (US); Jon A. Weidanz, Amarillo, TX (US); Hing C. Wong, Weston, FL (US); Elizabeth L. Thomson, Miami, FL (US)

(73) Assignee: Altor BioScience Corporation

( * ) Notice: Subject to any disclaimer, the term of this patent is extended or adjusted under 35 U.S.C. 154(b) by 477 days.

(21) Appl. No.: 10/163,084

(22) Filed: Jun. 5, 2002

(65) Prior Publication Data

US 2008/0269113 A1 Oct. 30, 2008

Related U.S. Application Data

(60) Provisional application No. 60/296,324, filed on Jun. 5, 2001.

(51) Int. Cl.
*C07K 16/30* (2006.01)
(52) U.S. Cl. .................. 530/388.22; 530/387.3
(58) Field of Classification Search ............ None
See application file for complete search history.

(56) References Cited

U.S. PATENT DOCUMENTS

| | | | |
|---|---|---|---|
| 4,867,973 | A | 9/1989 | Goers et al. |
| 5,057,313 | A | 10/1991 | Shih et al. |
| 5,106,955 | A | 4/1992 | Endo et al. |
| 5,164,311 | A | 11/1992 | Gupta |
| 5,830,755 | A | 11/1998 | Nishimura et al. |
| 5,990,275 | A | 11/1999 | Whitlow et al. |
| 6,015,556 | A | 1/2000 | Bagshawe |
| 6,399,368 | B1 | 6/2002 | Ward |
| 6,623,957 | B2 | 9/2003 | Ward |

FOREIGN PATENT DOCUMENTS

| | | | |
|---|---|---|---|
| WO | WO 93/24525 | A | 12/1993 |
| WO | WO 96/18409 | A | 6/1996 |
| WO | WO 00/23087 | | 4/2000 |

OTHER PUBLICATIONS

Mikayama et al. Molecular cloning and functional expression of a cDNA encoding glycosylation -inhibiting factor. PNAS, 1993. 90: 10056-10060.*
Lazar et al. Transforming growth factor alpha: Mutation of aspartic acid 47 and leucine 48 results in different biological activities. Mol. Cell. Biol. 1988; 8: 1247-1252.*
Skolnick et al. From genes to protein structure and function: novel applications of computational approaches in the genomic era. Trends in Biotech. 2000; 18(1): 34-39.*
Rudikoff et al. Single amino acid substitution altering antigen-binding specificity. Proc. Natl. Acad. Sci. 1982; 79: 1979-1983.*
Panka et. al. Variable region framework differences result in decreased or increased affinity of variant anti-digoxin antibodies. Proc. Natl. Acad. Sci. 1988; 85: 3080-3083.*

Theobald et.al. Targeting p53 as a general tumor antigen. PNAS. 1995; 92: 11993-11997.*
Chung et.al. Functional three-domain single-chain T-cell receptors. PNAS. 1994; 91: 12654-12658.*
MSN Encarta Dictionary. p. 1-2.*
Carding et al., Nat Rev Immunol. May 2002;2(5):336-45, in particular p. 338.*
Sykulev et al., Proc Natl Acad Sci U S A. Nov. 22, 1994;91(24):11487-91.*
Janeway et al., Immunobiology, 5th Ed., Garland Science, pp. 105-108 (2001).*
Chien et al., Proc Natl Acad Sci U S A. Jul. 1989;86(14):5532-6.*
Vajdos et al., J Mol Biol. Jul. 5, 2002;320(2):415-28.*
Colman P. M., Research in Immunology, 145:33-36, 1994.*
Liu, et al., "Targeting of Human p53-overexpressing Tumor Cells by an HLA A*0201-restricted Murine T-Cell Receptor Expressed in Jurkat T Cells[1]", Cancer Research 60, 693-701, Feb. 1, 2000.
Weidanz J. A. et al. "Display of Functional Alphabeta Single-Chain T-Cell Receptor Molecules On The Surface of Bacteriophage", Journal of Immunological Methods, Elsevier Science Publishers B.V., Amsterdam, NL, vol. 221, No. 1-2, Dec. 1998, pp. 59-76.
Theobald M. et al. "Targeting p53 As A General Tumor Antigen", Proceedings Of The National Academy of Sciences Of USA, National Academy Of Science, Washington, DC, US, vol. 92, Dec. 1995, pp. 11993-11997.
Hoffman, T. K. et al. "Generation Of T Cells Specific For The Wild-Type Sequence p53(264-272) Peptide In Cancer Patients: Implications For Immunoselection Of Epitope Loss Variants", Journal Of Immunology (Baltimore, MD.: 1950) Nov. 15, 2000, vol. 165, No. 10, pp. 5938-5944.
Theobald, M. et al. "The Sequence Alteration Associated With A Mutational Hotspot In p53Protects Cells From Lysis By Cytotoxic T Lymphocytes Specific For A Flanking Peptide Epitope", Journal Of Experimental Medicine, Tokyo, JP, vol. 188, No. 6, Sep. 21, 1998, pp. 1017-1028.
Gnjatic S. et al. "Mapping And Ranking Of Potential Cytotoxic T Epitopes In The p53 Protein: Effect Of Mutations And Polymorphism On Peptide Binding Topurified And Refolded HLA Molecules", European Journal Of Immunology, Weinheim, DE, vol. 25, Jun. 1, 1995, pp. 1638-1642.

(Continued)

*Primary Examiner*—Michail Belyavskyi
*Assistant Examiner*—Zachary Skelding
(74) *Attorney, Agent, or Firm*—Edwards Angell Palmer & Dodge LLP; Peter F. Corless; Jonathan M. Sparks

(57) ABSTRACT

The invention provides T-cell receptor (TCR) molecules comprising a Vα chain and a Vβ chain that bind peptides derived from the p53 protein, preferably, the human p53 protein. The TCR molecules include both heterodimeric molecules and single chain molecules which specifically bind a sequence preferably spanning about amino acid positions 264-272 of the p53 protein displayed in the context of an HLA molecule, preferably, HLA-A2.1. Also disclosed are methods for making and using such TCR molecules. The invention has a wide spectrum of useful application including therapeutic uses and use in the detection of cells expressing p53 protein.

23 Claims, 10 Drawing Sheets

OTHER PUBLICATIONS

Theobald, M. et al. "Tolerance To p53 By A2.1-Restricted Cytotoxic T Lymphocytes", Journal Of Experimental Medicine, Tokyo, JP, vol. 185, No. 5, 1997, pp. 833-841.

Card, Kimberllyn F. et al. A Soluble Single-Chain T-Cell Receptor IL-2 Fusion Protein Retains.

Kuball, Juergen et al. "Cooperation Of Human Tumor-Reactive CD4+ And CD8+ T Cells After Redirection Of Their Specificity By A High-Affinity P53A2.1-Specific TCR", Immunity, vol. 22, No. 1, Jan. 2005, pp. 117-129.

* cited by examiner

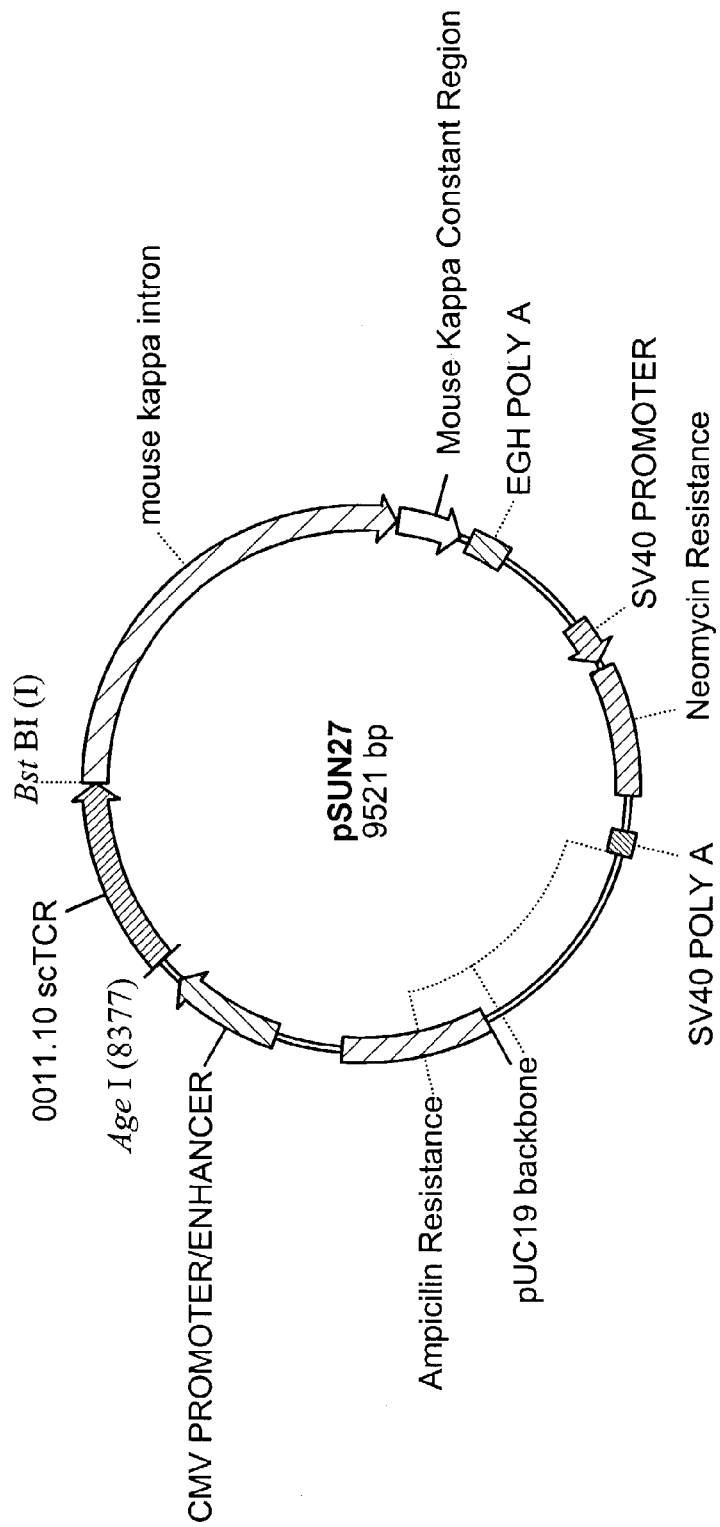

Vα3 domain

```
       Q S V T Q P D   A R V   T V S
  +1   CAGTCAGTGA CGCAGCCCGA TGCTCGCGTC ACTGTCTCTG
  51   GTCAGTCACT GCGTCGGGCT ACGAGGGCAG TGACAGAGAC

+1 E G A S   L Q L R C K Y   S Y S   G T P
 101   AAGGAGCCTC TCTGCAGCTG AGATGCAAGT ATTCCTACTC
       TGGGACACCT
       TTCCTCGGAG AGACGTCGAC TCTACGTTCA TAAGGATGAG
       ACCCTGTGGA

+1 Y L F W   Y V Q   Y P R   Q G L Q   L L L
 151   TATCTGTTCT GGTATGTCCA GTACCCGCGG CAGGGGCTGC
       AGCTGCTCCT
       ATAGACAAGA CCATACAGGT CATGGGCGCC GTCCCCGACG
       TCGACGAGGA
```

FIG. 4A-1

| FIG. 4A-1 |
|-----------|
| FIG. 4A-2 |
| FIG. 4A-3 |

FIG. 4A

+1  K Y Y S G D P V V Q   G V N   G F E
201 CAAGTACTAT TCAGGAGACC CAGTGGTTCA AGGAGTGAAT
    GGCTTCGAGG
    GTTCATGATA AGTCCCTCTGG GTCACCAAGT TCCTCACTTA
25  CCGAAGCTCC

+1  I A E F S K S N   S S F H   L R K   A S V
251 CTGAGTTCAG CAAGAGTAAC TCTTCCTTCC ACCTGCGGAA
    AGCCTCTGTG
    GACTCAAGTC GTTCTCATTG AGAAGGAAGG TGGACGCCTT
30  TCGGAGACAC

+1  H W S D   S A V   Y F C   V L S E D S N
301 CACTGGAGCG ACTCTGCTGT GTACTTCTGT GTTTGAGCG
    AGGATAGCAA
    GTGACCTCGC TGAGACGACA CATGAAGACA CAAACTCGC
35  TCCTATCGTT

+1  Y Q L I W G S   G T K   L I I   K P D
351 CTATCAGTTG ATCTGGGGCT CTGGGACCAA GCTAATTATA
    AAGCCAGACA
    GATAGTCAAC TAGACCCCGA GACCCTGGTT CGATTAATAT
45  TTCGGTCTGT
                                              SpeI
                                               ~

FIG. 4A-2

```
                    Linker Region
       +1 T S G G G  G G S G G G G  G S G G G  G G S
              SpeI
       401  CTAGTGGTGG CGGTGGCAGC GGGCGGTGGT GTTCCGGTGG
50     CGGCGGTCT
            GATCACCACC GCCACCGTCG CCGCCACCAC CAAGGCCACC
            GCCGCCAAGA Vb3 Domain
       +1 G G G G S S  S N S K V I Q T P R Y
                     XhoI
       451  GGCGGTGGCG GTTCCTCGAG CAATTCAAAA GTCATTCAGA
5      CTCCAAGATA
            CCGCCACCGC CAAGGAGCTC GTTAAGTTTT CAGTAAGTCT
            GAGGTTCTAT +1  L V K  G Q G Q  K A K  M R C I P E
       501  TCTGGGTGAAA GGGCAAGGAC AAAAAGCAAA GATGAGGTGT
10     ATCCCTGAAA
            AGACCACTTT CCCGTTCCTG TTTTCGTTT CTACTCCACA
            TAGGGACTTT
15
```

FIG. 4A-3

```
     +1 K G H P V V F W Y Q Q N K N N E F
    551 AGGGACATCC AGTTGTATTC TGGTATCAAC AAAATAAGAA
        CAATGAGTTT
        TCCCTGTAGG TCAACATAAG ACCATAGTTG TTTTATTCTT
        GTTACTCAAA

+1 K F L I N F Q N Q E V L Q Q I D M
    601 AAATTTTTGA TTAACTTTCA GAATCAAGAA GTTCTTCAGC
        AAATAGACAT
        TTTAAAAACT AATTGAAAGT CTTAGTTCTT CAAGAAGTCG
        TTTATCTGTA

+1 T E K R F S A E C P S N S P C S
    651 GACTGAAAAA CGATTCTCTG CTGAGTGTCC TTCAAACTCA
        CCTTGCAGCC
        CTGACTTTTT GCTAAGAGAC GACTCACAGG AAGTTTGAGT
        GGAACGTCGG

+1 L E I Q S S E A G D S A L Y L C A
    701 TAGAAATTCA GTCCCTCTGAG GCAGGAGACT CAGCACTGTA
        CCTCTGTGCC
        ATCTTTAAGT CAGGAGACTC CGTCCTCTGA GTCGTGACAT
        GGAGACACGG
```

FIG. 4B-1

| FIG. 4B-1 |
| FIG. 4B-2 |
| FIG. 4B-3 |

FIG. 4B

+1  S  S  S  L  S  G  G  G  T  E  V  F  F  G  K  G  T  R
751 AGCAGTCTGT CAGGGGGCGG CACAGAAGTT TTCTTTGGTA AAGGAACCAG
    TCGTCAGACA GTCCCCCGCC GTGTCTTCAA AAGAAACCAT TTCCTTGGTC

Cb domain

+1  L  T  V  V  E  D  L  R  N  V  T  P  P  K  V  S
801 ACTCACAGTT GTAGAGGATC TGAGAAATGT GACTCCACCC AAGGTCTCCT
    TGAGTGTCAA CATCTCCTAG ACTCTTTACA CTGAGGTGGG TTCCAGAGGA

+1  L  F  E  P  S  K  A  E  I  A  N  K  Q  K  A  T  L
851 TGTTTGAGCC ATCAAAAGCA GAGATTGCAA ACAAACAAAA GGCTACCCTT
    ACAAACTCGG TAGTTTTCGT CTCTAACGTT TGTTTGTTTT CCGATGGGAA

+1  I  V  C  L  A  R  G  F  F  P  D  H  V  E  L  S  W  W
901 GTGTGCTTGG CCAGGGGCTT CTTCCCTGAC CACGTGGAGC TGAGCTGGTG
    CACACGAACC GGTCCCCGAA GAAGGGACTG GTGCACCTCG ACTCGACCAC

FIG. 4B-2

+1  V  N  G  K  E  V  H  S  G  V  S  T  D  P  Q  A
951 GGTGAATGGC AAGGAAGTCC ACAGTGGGGT CAGCACGGAC
CCTCAGGCCT CCACTTACCG TTCCTTCAGG TGTCACCCCA GTCGTGCCTG
GGAGTCCGGA

+1  Y  K  E  S  N  Y  S  Y  C  L  S  S  R  L  R  V  S
1001 ACAAGGAGAG CAATTATAGC TACTGCCTGA GCAGCCGCCT
GAGGGTCTCT TGTTCCTCTC GTTAATATCG ATGACGGACT CGTCGGCGGA
CTCCCAGAGA

+1  A  T  F  W  H  N  P  R  N  H  F  R  C  Q  V  Q  F
1051 GCTACCTTCT GGCACAATCC TCGCAACCAC TTCCGCTGCC
AAGTGCAGTT CGATGGAAGA CCGTGTTAGG AGCGTTGGTG AAGGCGACGG
TTCACGTCAA

+1  H  G  L  S  E  E  D  K  W  P  E  G  S  P  K  P
1101 CCATGGGCTT TCAGAGGAGG ACAAGTGGCC AGAGGGCTCA
CCCAAACCTG GGTACCCGAA AGTCCTCCTCC TGTTCACCGG TCTCCCGAGT
GGGTTTGGAC

1151 TCACACAGAA CATCAGTGCA GAGGCCTGGG GCCGAGCAGA C
     AGTGTGTCTT GTAGTCACGT CTCCGGACCC CGGGTCGTCT G

FIG. 4C

```
          I   Q   N   P   E   P   A   V   Y   Q   L
K   D   P   R   S   Q   D   S   T   L
ATCCAGAACCCAGAACCTGCTGTGTACCAGTAAAAGATCCTCGGTCTCAGGA
CAGCACCCTC

C   L   F   T   D   F   D   S   Q   I   N   V
P   K   T   M   E   S   G   T   F
TGCCTGTTCACCGACTTTGACTCCCAAATCAATGTGCCGAAAACCATGGAATC
TGGAACGTTC

I   T   D   K   T   V   L   D   M   K   A   M
D   S   K   S   N   G   A   I   A
ATCACTGACAAAACTGTCGTGGACATGAAAGCTATGGATTCCAAGAGCAATGG
GGCCATTGC

W   S   N   Q   T   S   F   T   C   Q   D
I   F   K   E   T   N   A   T   Y
CTGGAGCAACCAGACAAGCTTCACCTGCCAAGATATCTTCAAAGAGACCAAC
GCCACCTACC

P   S   S   D   V   P   S
CCAGTTCAGACGTTCCCAGT
```

FIG. 5

SEQUENCE LISTING

```
<160> NUMBER OF SEQ ID NOS: 23

<210> SEQ ID NO 1
<211> LENGTH: 9
<212> TYPE: PRT
<213> ORGANISM: Homo sapiens

<400> SEQUENCE: 1

Leu Leu Gly Arg Asn Ser Phe Glu Val
 1               5

<210> SEQ ID NO 2
<211> LENGTH: 377
<212> TYPE: PRT
<213> ORGANISM: Homo sapiens

<400> SEQUENCE: 2

Gln Ser Val Thr Gln Pro Asp Ala Arg Val Thr Val Ser Glu Gly Ala
 1               5                  10                  15

Ser Leu Gln Leu Arg Cys Lys Tyr Ser Tyr Ser Gly Thr Pro Tyr Leu
            20                  25                  30

Phe Trp Tyr Val Gln Tyr Pro Arg Gln Gly Leu Gln Leu Leu Leu Lys
        35                  40                  45

Tyr Tyr Ser Gly Asp Pro Val Val Gln Gly Val Asn Gly Phe Glu Ala
    50                  55                  60

Glu Phe Ser Lys Ser Asn Ser Ser Phe His Leu Arg Lys Ala Ser Val
65                  70                  75                  80
```

```
His Trp Ser Asp Ser Ala Val Tyr Phe Cys Val Leu Ser Glu Asp Ser
                 85                  90                  95

Asn Tyr Gln Leu Ile Trp Gly Ser Gly Thr Lys Leu Ile Ile Lys Pro
            100                 105                 110

Asp Thr Ser Gly Gly Gly Ser Gly Gly Gly Ser Gly Gly Gly
        115                 120                 125

Gly Ser Gly Gly Gly Ser Ser Ser Asn Ser Lys Val Ile Gln Thr
130                 135                 140

Pro Arg Tyr Leu Val Lys Gly Gln Gln Lys Ala Lys Met Arg Cys
145                 150                 155                 160

Ile Pro Glu Lys Gly His Pro Val Val Phe Trp Tyr Gln Gln Asn Lys
                165                 170                 175

Asn Asn Glu Phe Lys Phe Leu Ile Asn Phe Gln Asn Gln Glu Val Leu
            180                 185                 190

Gln Gln Ile Asp Met Thr Glu Lys Arg Phe Ser Ala Glu Cys Pro Ser
        195                 200                 205

Asn Ser Pro Cys Ser Leu Glu Ile Gln Ser Ser Glu Ala Gly Asp Ser
210                 215                 220

Ala Leu Tyr Leu Cys Ala Ser Ser Leu Ser Gly Gly Gly Thr Glu Val
225                 230                 235                 240

Phe Phe Gly Lys Gly Thr Arg Leu Thr Val Val Glu Asp Leu Arg Asn
                245                 250                 255

Val Thr Pro Pro Lys Val Ser Leu Phe Glu Pro Ser Lys Ala Glu Ile
            260                 265                 270

Ala Asn Lys Gln Lys Ala Thr Leu Val Cys Leu Ala Arg Gly Phe Phe
        275                 280                 285

Pro Asp His Val Glu Leu Ser Trp Trp Val Asn Gly Lys Glu Val His
290                 295                 300

Ser Gly Val Ser Thr Asp Pro Gln Ala Tyr Lys Glu Ser Asn Tyr Ser
305                 310                 315                 320

Tyr Cys Leu Ser Ser Arg Leu Arg Val Ser Ala Thr Phe Trp His Asn
                325                 330                 335

Pro Arg Asn His Phe Arg Cys Gln Val Gln Phe His Gly Leu Ser Glu
            340                 345                 350

Glu Asp Lys Trp Pro Glu Gly Ser Pro Lys Pro Val Thr Gln Asn Ile
        355                 360                 365

Ser Ala Glu Ala Trp Gly Arg Ala Asp
370                 375

<210> SEQ ID NO 3
<211> LENGTH: 90
<212> TYPE: PRT
<213> ORGANISM: Homo sapiens

<400> SEQUENCE: 3

Ile Gln Asn Pro Glu Pro Ala Val Tyr Gln Leu Lys Asp Pro Arg Ser
  1               5                  10                  15

Gln Asp Ser Thr Leu Cys Leu Phe Thr Asp Phe Asp Ser Gln Ile Asn
             20                  25                  30

Val Pro Lys Thr Met Glu Ser Gly Thr Phe Ile Thr Asp Lys Thr Val
         35                  40                  45

Leu Asp Met Lys Ala Met Asp Ser Lys Ser Asn Gly Ala Ile Ala Trp
     50                  55                  60

Ser Asn Gln Thr Ser Phe Thr Cys Gln Asp Ile Phe Lys Glu Thr Asn
 65                  70                  75                  80
```

```
Ala Thr Tyr Pro Ser Ser Asp Val Pro Ser
            85                  90

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Linker
      peptide

<400> SEQUENCE: 4

Ala Ser Gly Gly Gly Gly Ser Gly Gly Gly
  1               5                  10

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 5

Gly Gly Gly Gly Ser
  1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide tag

<400> SEQUENCE: 6

Glu Glu Glu Glu Tyr Met Pro Met Glu
  1               5

<210> SEQ ID NO 7
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gaggtggccc agccggccat ggcccagtca gtgacgcagc                    40

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gaggtgacta gtgtctggct ttataattag                               30

<210> SEQ ID NO 9
<211> LENGTH: 40
<212> TYPE: DNA
<213> ORGANISM: Artificial Sequence
<220> FEATURE:
<223> OTHER INFORMATION: Description of Artificial Sequence: Synthetic
``` oligonucleotide

<400> SEQUENCE: 9
gaggtggccc agccggccat ggccgagcag gtggagcagc    40

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
gaggtgacta gtgtttgatt taacagagag    30

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11 gggggggctcg agcaattcaa aagtcattca gactc    35

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
gaggtggagc ccggggtctg ctcggcccca ggc    33

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cccaccggtc agtcagtgac gcagccc    27

<210> SEQ ID NO 14
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
gtggagttcg aaaagtgtac ttacgtttgt ctgctcggcc ccag    44

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 15
cccaccggtg agcaggtgga gcagctt                                        27

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
gaggtgaccg gtcagtcagt gacgcagc                                       28

<210> SEQ ID NO 17
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gtggagatcg ataagtgtac ttacgttttc attatcgcga tccggagtta acgtctgctc    60
ggccccag                                                             68

<210> SEQ ID NO 18
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
gaggtgaccg gtgagcaggt ggagcagc                                       28

<210> SEQ ID NO 19
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gaggtggtta acgatcccaa actctgctac ttgctagatg gaatcctc                 48

<210> SEQ ID NO 20
<211> LENGTH: 46
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
gaggtgatcg ataagtgtac ttacgttttt agcgaggggg cagggc                   46

<210> SEQ ID NO 21
<211> LENGTH: 1131
<212> TYPE: DNA
<213> ORGANISM: Homo sapiens
<220> FEATURE:
<221> NAME/KEY: CDS
```

-continued

<222> LOCATION: (1)..(1131)

<400> SEQUENCE: 21

| | | | | | | | | | | | | | | | | |
|---|---|---|---|---|---|---|---|---|---|---|---|---|---|---|---|---|
| cag | tca | gtg | acg | cag | ccc | gat | gct | cgc | gtc | act | gtc | tct | gaa | gga | gcc | 48 |
| Gln | Ser | Val | Thr | Gln | Pro | Asp | Ala | Arg | Val | Thr | Val | Ser | Glu | Gly | Ala | |
| 1 | | | | 5 | | | | | 10 | | | | | 15 | | |
| tct | ctg | cag | ctg | aga | tgc | aag | tat | tcc | tac | tct | ggg | aca | cct | tat | ctg | 96 |
| Ser | Leu | Gln | Leu | Arg | Cys | Lys | Tyr | Ser | Tyr | Ser | Gly | Thr | Pro | Tyr | Leu | |
| | | | 20 | | | | | 25 | | | | | 30 | | | |
| ttc | tgg | tat | gtc | cag | tac | ccg | cgg | cag | ggg | ctg | cag | ctg | ctc | ctc | aag | 144 |
| Phe | Trp | Tyr | Val | Gln | Tyr | Pro | Arg | Gln | Gly | Leu | Gln | Leu | Leu | Leu | Lys | |
| | | 35 | | | | | 40 | | | | | 45 | | | | |
| tac | tat | tca | gga | gac | cca | gtg | gtt | caa | gga | gtg | aat | ggc | ttc | gag | gct | 192 |
| Tyr | Tyr | Ser | Gly | Asp | Pro | Val | Val | Gln | Gly | Val | Asn | Gly | Phe | Glu | Ala | |
| | 50 | | | | | 55 | | | | | 60 | | | | | |
| gag | ttc | agc | aag | agt | aac | tct | tcc | ttc | cac | ctg | cgg | aaa | gcc | tct | gtg | 240 |
| Glu | Phe | Ser | Lys | Ser | Asn | Ser | Ser | Phe | His | Leu | Arg | Lys | Ala | Ser | Val | |
| 65 | | | | | 70 | | | | | 75 | | | | | 80 | |
| cac | tgg | agc | gac | tct | gct | gtg | tac | ttc | tgt | gtt | ttg | agc | gag | gat | agc | 288 |
| His | Trp | Ser | Asp | Ser | Ala | Val | Tyr | Phe | Cys | Val | Leu | Ser | Glu | Asp | Ser | |
| | | | | 85 | | | | | 90 | | | | | 95 | | |
| aac | tat | cag | ttg | atc | tgg | ggc | tct | ggg | acc | aag | cta | att | ata | aag | cca | 336 |
| Asn | Tyr | Gln | Leu | Ile | Trp | Gly | Ser | Gly | Thr | Lys | Leu | Ile | Ile | Lys | Pro | |
| | | | 100 | | | | | 105 | | | | | 110 | | | |
| gac | act | agt | ggt | ggc | ggt | ggc | agc | ggc | ggt | ggt | ggt | tcc | ggt | ggc | ggc | 384 |
| Asp | Thr | Ser | Gly | Gly | Gly | Gly | Ser | Gly | Gly | Gly | Gly | Ser | Gly | Gly | Gly | |
| | | 115 | | | | | 120 | | | | | 125 | | | | |
| ggt | tct | ggc | ggt | ggc | ggt | tcc | tcg | agc | aat | tca | aaa | gtc | att | cag | act | 432 |
| Gly | Ser | Gly | Gly | Gly | Gly | Ser | Ser | Ser | Asn | Ser | Lys | Val | Ile | Gln | Thr | |
| | 130 | | | | | 135 | | | | | 140 | | | | | |
| cca | aga | tat | ctg | gtg | aaa | ggg | caa | gga | caa | aaa | gca | aag | atg | agg | tgt | 480 |
| Pro | Arg | Tyr | Leu | Val | Lys | Gly | Gln | Gly | Gln | Lys | Ala | Lys | Met | Arg | Cys | |
| 145 | | | | | 150 | | | | | 155 | | | | | 160 | |
| atc | cct | gaa | aag | gga | cat | cca | gtt | gta | ttc | tgg | tat | caa | caa | aat | aag | 528 |
| Ile | Pro | Glu | Lys | Gly | His | Pro | Val | Val | Phe | Trp | Tyr | Gln | Gln | Asn | Lys | |
| | | | | 165 | | | | | 170 | | | | | 175 | | |
| aac | aat | gag | ttt | aaa | ttt | ttg | att | aac | ttt | cag | aat | caa | gaa | gtt | ctt | 576 |
| Asn | Asn | Glu | Phe | Lys | Phe | Leu | Ile | Asn | Phe | Gln | Asn | Gln | Glu | Val | Leu | |
| | | | 180 | | | | | 185 | | | | | 190 | | | |
| cag | caa | ata | gac | atg | act | gaa | aaa | cga | ttc | tct | gct | gag | tgt | cct | tca | 624 |
| Gln | Gln | Ile | Asp | Met | Thr | Glu | Lys | Arg | Phe | Ser | Ala | Glu | Cys | Pro | Ser | |
| | | 195 | | | | | 200 | | | | | 205 | | | | |
| aac | tca | cct | tgc | agc | cta | gaa | att | cag | tcc | tct | gag | gca | gga | gac | tca | 672 |
| Asn | Ser | Pro | Cys | Ser | Leu | Glu | Ile | Gln | Ser | Ser | Glu | Ala | Gly | Asp | Ser | |
| | 210 | | | | | 215 | | | | | 220 | | | | | |
| gca | ctg | tac | ctc | tgt | gcc | agc | agt | ctg | tca | ggg | ggc | ggc | aca | gaa | gtt | 720 |
| Ala | Leu | Tyr | Leu | Cys | Ala | Ser | Ser | Leu | Ser | Gly | Gly | Gly | Thr | Glu | Val | |
| 225 | | | | | 230 | | | | | 235 | | | | | 240 | |
| ttc | ttt | ggt | aaa | gga | acc | aga | ctc | aca | gtt | gta | gag | gat | ctg | aga | aat | 768 |
| Phe | Phe | Gly | Lys | Gly | Thr | Arg | Leu | Thr | Val | Val | Glu | Asp | Leu | Arg | Asn | |
| | | | | 245 | | | | | 250 | | | | | 255 | | |
| gtg | act | cca | ccc | aag | gtc | tcc | ttg | ttt | gag | cca | tca | aaa | gca | gag | att | 816 |
| Val | Thr | Pro | Pro | Lys | Val | Ser | Leu | Phe | Glu | Pro | Ser | Lys | Ala | Glu | Ile | |
| | | | 260 | | | | | 265 | | | | | 270 | | | |
| gca | aac | aaa | caa | aag | gct | acc | ctt | gtg | tgc | ttg | gcc | agg | ggc | ttc | ttc | 864 |
| Ala | Asn | Lys | Gln | Lys | Ala | Thr | Leu | Val | Cys | Leu | Ala | Arg | Gly | Phe | Phe | |
| | | 275 | | | | | 280 | | | | | 285 | | | | |
| cct | gac | cac | gtg | gag | ctg | agc | tgg | tgg | gtg | aat | ggc | aag | gaa | gtc | cac | 912 |
| Pro | Asp | His | Val | Glu | Leu | Ser | Trp | Trp | Val | Asn | Gly | Lys | Glu | Val | His | |
| | 290 | | | | | 295 | | | | | 300 | | | | | |

```
agt ggg gtc agc acg gac cct cag gcc tac aag gag agc aat tat agc      960
Ser Gly Val Ser Thr Asp Pro Gln Ala Tyr Lys Glu Ser Asn Tyr Ser
305                 310                 315                 320 tac tgc ctg agc agc cgc ctg agg gtc tct gct acc ttc tgg cac aat     1008
Tyr Cys Leu Ser Ser Arg Leu Arg Val Ser Ala Thr Phe Trp His Asn
                325                 330                 335 cct cgc aac cac ttc cgc tgc caa gtg cag ttc cat ggg ctt tca gag     1056
Pro Arg Asn His Phe Arg Cys Gln Val Gln Phe His Gly Leu Ser Glu
            340                 345                 350 gag gac aag tgg cca gag ggc tca ccc aaa cct gtc aca cag aac atc     1104
Glu Asp Lys Trp Pro Glu Gly Ser Pro Lys Pro Val Thr Gln Asn Ile
        355                 360                 365 agt gca gag gcc tgg ggc cga gca gac                                 1131
Ser Ala Glu Ala Trp Gly Arg Ala Asp
    370                 375

<210> SEQ ID NO 22
<211> LENGTH: 270
<212> TYPE: DNA
<213> ORGANISM: Homo sapiens
<220> FEATURE:
<221> NAME/KEY: CDS
<222> LOCATION: (1)..(270)

<400> SEQUENCE: 22 atc cag aac cca gaa cct gct gtg tac cag tta aaa gat cct cgg tct       48
Ile Gln Asn Pro Glu Pro Ala Val Tyr Gln Leu Lys Asp Pro Arg Ser
1               5                   10                  15 cag gac agc acc ctc tgc ctg ttc acc gac ttt gac tcc caa atc aat       96
Gln Asp Ser Thr Leu Cys Leu Phe Thr Asp Phe Asp Ser Gln Ile Asn
                20                  25                  30 gtg ccg aaa acc atg gaa tct gga acg ttc atc act gac aaa act gtg      144
Val Pro Lys Thr Met Glu Ser Gly Thr Phe Ile Thr Asp Lys Thr Val
            35                  40                  45 ctg gac atg aaa gct atg gat tcc aag agc aat ggg gcc att gcc tgg      192
Leu Asp Met Lys Ala Met Asp Ser Lys Ser Asn Gly Ala Ile Ala Trp
        50                  55                  60 agc aac cag aca agc ttc acc tgc caa gat atc ttc aaa gag acc aac      240
Ser Asn Gln Thr Ser Phe Thr Cys Gln Asp Ile Phe Lys Glu Thr Asn
65                  70                  75                  80 gcc acc tac ccc agt tca gac gtt ccc agt                              270
Ala Thr Tyr Pro Ser Ser Asp Val Pro Ser
                85                  90

<210> SEQ ID NO 23
<211> LENGTH: 20
<212> TYPE: PRT
<213> ORGANISM: Artificial Sequence
<220> FEATURE:
<223> OTHER INFORMATION: Description of Artificial Sequence: Linker
      peptide

<400> SEQUENCE: 23

Gly Gly Gly Gly Ser Gly Gly Gly Ser Gly Gly Gly Gly Ser Gly
1               5                   10                  15

Gly Gly Gly Ser
            20
```

P53 BINDING T CELL RECEPTOR MOLECULES

RELATED APPLICATIONS

This application claims claims the benefit of U.S. Provisional Application 60/296,324, filed Jun. 5, 2001, the contents of which is expressly incorporated herein by reference.

GOVERNMENT SUPPORT

This invention was made with government support under Contract No. CA 25803 by the National Institutes of Health. The government has certain rights in this invention.

FIELD OF INVENTION

The present invention relates to T cell receptor (TCR) molecules that bind particular p53 protein sequences as well as methods for making and using such molecules. The TCR molecules of the invention are useful for a variety of applications including therapeutic and diagnostic purposes.

BACKGROUND OF THE INVENTION

Traditional approaches to the treatment of diseases such as cancer have included surgery, radiation, chemotherapy, antibiotics or combination therapies. However, such therapies have not proven effective against a majority of these indications. Development of alternate remedies for preventing and/or treating such human diseases is crucial. In recent years immunotherapy and gene therapy approaches utilizing antibodies and T-lymphocytes have emerged as new and promising methods for treating human disease.

One such approach to treatment has included the use of antibodies for targeting of therapeutic or diagnostic agents to particular targets. Numerous groups have made developments revolving around the use of antibodies as a targeting agent. Such developments have included construction of antibody fusion proteins and antibody conjugate molecules linking antibodies to various effector molecules, including radioactive molecules, chemotherapeutics agents, toxins, and additional bioactive proteins. Therapeutics or diagnostics developed using such molecules are designed to cause a particular effect which is targeted by the linked antibody.

Just as antibodies have been developed as therapeutics, additional primary effectors of the immune system, T cell receptors (TCR), have unique advantages as a platform for developing therapeutics. While antibodies are limited to recognition of pathogens in the blood and extracellular spaces or to protein targets on the cell surface, T cell receptors can recognize antigens displayed with MHC molecules on the surfaces of cells (including antigens derived from intracellular proteins). Depending on the subtype of T cells that recognize displayed antigen and become activated, T cell receptors and T cells harboring T cell receptors can participate in controlling various immune responses. For instance, T cells are involved in regulation of the humoral immune response through induction of differentiation of B cells into antibody producing cells. In addition, activated T cells act to initiate cell-mediated immune responses. Thus, T cell receptors can recognize additional targets not available to antibodies.

A T cell response is modulated by antigen binding to a T cell receptor molecule. One type of TCR is a membrane bound heterodimer consisting of an α chain and a β chain resembling an immunoglobin variable (V) and constant (C) region. The TCR α chain includes a covalently linked Vα and Cα chain, whereas the β chain includes a Vβ chain covalently linked to a Cβ chain. The Vα and Vβ chains form a pocket or cleft that can bind a superantigen or antigen in the context of a major histocompatibility complex (MHC) (known in humans as an HLA complex). See generally Davis, *Ann. Rev. of Immunology* 3: 537 (1985); *Fundamental Immunology* 3rd Ed., W. Paul Ed. Raven Press LTD. New York (1993).

The TCR is believed to play an important role in the development and function of the immune system. For example, the TCR has been reported to mediate cell killing, increase B cell proliferation, and impact the development and severity of various disorders including cancer, allergies, viral infections and autoimmune disorders.

Human p53 has been reported to be a tumor suppressor protein and peptide epitopes from p53 are presented by particular class I MHC molecules. p53 has been further reported to be a candidate for a broad-spectrum, tumor-associated cytotoxic T-cell (CTL) target. See, e.g., Theobald, M. et. al. (1995) *PNAS (USA)* 92: 11993 and references cited therein.

There is recognition that abnormal forms of the human p53 protein are associated with a wide variety of cancers. One belief is that the abnormal or mutated version overrides the protective features of normal (wild-type) p53 protein. See, e.g., Levine, A. J. et. al. (1991) *Nature (London)* 351: 453.

Human class I molecules that recognize and specifically bind peptides derived from human p53 protein have been described. One such molecule is HLA-A2.1. See, Theobald, M. et. al., supra.

It would be desirable to have TCR molecules that recognize and bind peptides derived from the human p53 protein. It would be especially desirable to have heterodimeric and single chain TCR molecules that specifically bind sequence spanning about amino acid positions 264 to 272 of the human p53 protein.

SUMMARY OF THE INVENTION

We have now identified T-cell receptor (TCR) molecules that bind peptides derived from the human p53 protein. In one aspect, we have isolated heterodimeric TCR molecules that specifically bind sequence preferably spanning about amino acid positions 264 to 272 of the human p53 protein displayed in the context of an HLA molecule, preferably, HLA-A2.1. In another aspect, we have made single chain TCR (sc-TCR) molecules that specifically bind the same sequence. Also disclosed are methods for making and using such TCR molecules. The invention has a wide spectrum of useful applications including therapeutic uses and use in the detection of cells expressing p53 protein.

TCR molecules in accord with the invention are typically heterodimers or single chain molecules that bind sequence preferably spanning between from about amino acid positions 264 to 272 of the human p53 molecule. An especially preferred sequence is the Leu Leu Gly Arg Asn Ser Phe Glu Val (SEQ ID NO. 1) epitope that spans amino acid positions 264 to 272 of the human p53 molecule. Other suitable p53 sequences are provided below.

Particular TCR molecules feature a variety of useful activities. For example, the heterodimeric TCR molecules disclosed herein can be used to detect cell expression of p53 protein, especially in the context of an appropriate antigen-presenting complex. An illustration of such a complex is a primate class I major histocompatibility complex (MHC) that binds and presents to CTLs immunologically relevant fragments of the p53 protein. A preferred class I MHC molecule is the human HLA-A2.1 complex disclosed below.

The invention encompasses a variety of heterodimeric TCR molecules whose context is usually pre-determined to suit an intended use. For example, in one embodiment, heterodimeric TCR molecules are expressed as cell surface molecules on a transfected or genetically engineered recombinant cell. Examples of the cells are provided below. Additionally suitable heterodimeric TCR molecules are provided in a more soluble format, e.g., heterodimers that include one or more immunoglobin (Ig) sequences as discussed below.

More particular heterodimeric TCR molecules of the invention feature an α chain and a β chain which chains are typically linked together via one or more covalent bonds. Preferably, such covalent bonds include one or more disulfide linkages. More preferred heterodimers include at least one Vα chain and at least one Vβ chain which chains preferably configure to effectively position, within or near the heterodimer binding cleft, sequence spanning about amino acid positions 264 to 272 of the human p53 molecule, preferably amino acid positions 264 to 272. By the phrase "effectively position" is meant that TCR V chains according to the invention (heterodimer or single chain format) associate to bind a specific p53 sequence as determined by the standard assays disclosed herein including preferred T cell binding and ELISA tests provided below.

More specific V chains of the heterodimeric TCRs include the V-α chain linked covalently to a C-α chain and the V-β chain linked to a C-β chain. In most embodiments, the C-α chain and C-β chain are each independently linked to a suitable cell transmembrane domain which domain is typically further linked independently to a suitable cytosolic domain. In instances in which soluble heterodimeric molecules are desired, it may be more preferable to remove at least the transmembrane domain, preferably essentially all of the transmembrane domain using, e.g., standard recombinant DNA manipulations.

The invention features other useful TCR molecules including the single chain T cell receptor (sc-TCR) molecules disclosed herein. Such molecules generally include at least one Vα chain bound, by at least one peptide sequence, to at least one Vβ chain. If desired, the sc-TCR can further include at least one Cα chain fragment and optionally at least one Cβ chain fragment. In more particular invention embodiments, the sc-TCR will include about one Vα chain bound to about one Vβ chain by at least one peptide linker sequence. The arrangement of any V or C sequence in the sc-TCRs is not usually important so long as intended binding results are achieved. However, it is generally preferred that the Vα and Vβ chains be sufficient to effectively bind to the human p53 sequence spanning about amino acid positions 264 to 272 as determined by standard binding tests.

The present invention provides important advantages.

For example, the heterodimeric and single chain TCRs provide, for the first time, TCR molecules that recognize and bind an important p53 epitope sequence. Binding of that sequence by the molecules of the invention provides for important and reliable recognition of p53 tumor suppressor protein in cancerous or pre-cancerous cells. Thus, in one invention aspect, the molecules can be used diagnostically to detect, and quantify if desired, presence and amount of p53 in cells, tissue and organs. Such cells include cultured cells as well as primary, secondary and immortalized cell lines. The ability to detect p53 protein is highly useful as a cancer diagnostic in vitro and in vivo. Alternatively, the TCR molecules of the invention can be used to detect and optionally quantify p53 expression in cells, particularly those that can present the p53 antigen in the context of a suitable MHC class I molecule, preferably the HLA-A2.1 complex.

Accordingly, and in one aspect, the invention features an isolated T cell receptor (TCR) heterodimer that includes a Vα chain and a Vβ chain. Preferably, the heterodimer is capable of binding, preferably specifically in the context of an HLA-A2.1 MHC molecule, the following "target" amino acid sequence: Leu Leu Gly Arg Asn Ser Phe Glu Val (SEQ ID NO. 1) including variants of that sequence having at least one conservative amino acid replacement. Preferred binding is determined by any standard TCR binding assay where binding specificity is indicated as an increase in binding which is significantly different from binding to an irrelevant (control) TCR (where "significance" is determined using routine statistical methods known in the art, e.g., with p≦0.05). Preferably, binding is at least about 2-fold, at least about 10-fold, at least about 20-fold, at least about 50-fold, or at least about 100-fold higher than control values. A specifically preferred TCR binding assay and irrelevant TCR heterodimer are disclosed below.

In a more specific embodiment, the invention features an isolated T-cell receptor (TCR) heterodimer that includes an α-chain and a β-chain in which the α-chain comprises covalently linked in sequence: a) a Vα chain and b) a Cα chain; and the β-chain comprises covalently linked in sequence: c) a Vβ chain and a Cβ sequence. Preferably, the heterodimer is capable of binding, in the context of an HLA-A2.1 MHC molecule, the foregoing target amino acid of SEQ ID NO. 1 as well as variants of that target sequence that have at least one conservative amino acid replacement.

As discussed, the invention also features sc-TCR molecules that include V chains capable of specifically binding the target sequence of SEQ ID NO: 1.

In one embodiment, such sc-TCRs include at least one Vα chain covalently linked to at least one Vβ chain by at least one peptide linker sequence. Preferably, such sc-TCRs include between from about one to five of such V chains, more preferably about one to two of such V chains. Also preferably, such V chains will be linked together by between from about one to five peptide linkers, more preferably about one to two of such linkers. A more preferred sc-TCR is capable of binding, in the context of an HLA-A2.1 MHC molecule, the following target amino acid sequence: Leu Leu Gly Arg Asn Ser Phe Glu Val (SEQ ID NO. 1) including variants of that sequence having at least one conservative amino acid replacement.

Preferred binding is determined by any standard TCR binding assay where binding specificity is indicated as an increase in binding which is significantly different from binding to an irrelevant (control) TCR (where "significance" is determined using routine statistical methods known in the art, e.g., with p≦0.05). Preferably, binding is at least about 2-fold, at least about 10-fold, at least-about 20-fold, at least about 50-fold, or at least about 100-fold higher than control values. A specifically preferred sc-TCR binding assay and irrelevant sc-TCR are disclosed below.

In another aspect, the invention features at least a pair of nucleic acid segments (typically DNA or RNA) that encode one or more of the heterodimers provided herein.

In another aspect, the invention encompasses a DNA vector that includes at least one of the DNA segments encoding the TCR heterodimers. For example, a first DNA segment can encode the α chain and a second DNA segment can encode the β chain. In some instances, it may be more desirable to provide a single DNA vector with segments that encode both the α and β chains of the heterodimer.

Also envisioned are cells that include the DNA vectors disclosed herein.

The invention also features a nucleic acid segment (DNA or RNA) that encodes at least one, preferably between from about one to five, more preferably about one to two, of the sc-TCR molecules provided herein. Also included are DNA vectors that include the nucleic acid segment.

In another aspect, the invention features methods for identifying a cell or tissue expressing p53 protein in the context of an HLA-A2.1 MHC molecule. In one embodiment, such methods include contacting the cell or tissue with a transduced or genetically engineered recombinant cell comprising the sc-TCR or TCR heterodimers disclosed herein. Alternatively, the cell or tissue can be contacted with a soluble sc-TCR or a TCR heterodimer instead of (or in combination with) the transduced or genetically engineered cell expressing the sc-TCR or TCR heterodimer.

The invention also features methods for identifying cells or tissues expressing p53 protein in the context of an HLA-A2.1 MHC molecule. In preferred examples of the invention, the methods include contacting the cell or tissue with a sc-TCR as provided herein.

Also encompassed by the present invention are methods for killing a cell expressing the following target amino acid sequence: Leu Leu Gly Arg Asn Ser Phe Glu Val (SEQ ID NO. 1) including variants of that sequence having at least one conservative amino acid replacement. More particular methods include contacting the cell with a transduced or recombinant cell expressing a sc-TCR or heterodimeric TCR molecule as provided herein. Additionally preferred methods further include contacting the cell with an amount of sc-TCR or heterodimeric TCR that is generally sufficient to injure or kill the cell as determined by conventional assays (e.g., trypan blue exclusion, presence of apoptotic features, etc.).

In another aspect, the present invention features methods for treating cancer that include administering to a mammal a therapeutically effective amount of at least one of: a) a transduced or genetically engineered recombinant cell comprising a TCR heterodimer as provided herein or b) at least one of the sc-TCRs of the invention, preferably one of such sc-TCRs. Preferably, the cancer is characterized by upregulation of p53 protein by at least about two-fold, preferably at least five to 10 fold, preferably about 100 fold as determined by standard immunohistochemistry or flow cytometery as discussed below.

Other aspects and embodiments of the invention are discussed infra.

BRIEF DESCRIPTION OF THE DRAWINGS

FIG. 2 is a schematic drawing showing the pSUN27 vector (deposited as ATCC #209276).

FIG. 3 is a schematic drawing showing regions of the vectors encoding preferred bispecific hybrid molecules pBISP/D011.10 and pBISP/149 (deposited as ATCC #203186 with the designation pSUN28).

FIGS. 4A1-3 (nucleotides 1-489 of SEQ ID NO:21, coding residues 1-163 of SEQ ID NO:2), 4B1-3 (nucleotides 490-1089 of SEQ ID NO:21, coding residues 164-363 of SEQ ID NO:2), and 4C (nucleotides 1090-1131 of SEQ ID NO:21, coding residues 364-377 of SEQ ID NO:2) are drawings showing the amino acid and nucleic acid sequences of the 264 single chain TCR (264 sc-TCR) (SEQ ID NO:2). Vα3=TCR Vα3 domain (amino acids 61-399); Linker sequence (amino acids 400-471); Vb3=TCR Vβ 3 domain (amino acids 472-813); Cb=TCR Cβ domain (amino acids 472-813).

FIG. 5 is a drawing showing the optional Cα domain (SEQ ID NO. 3) of the 264 TCR coded for by SEQ ID NO: 22.

DETAILED DESCRIPTION OF THE INVENTION

Figure 1:
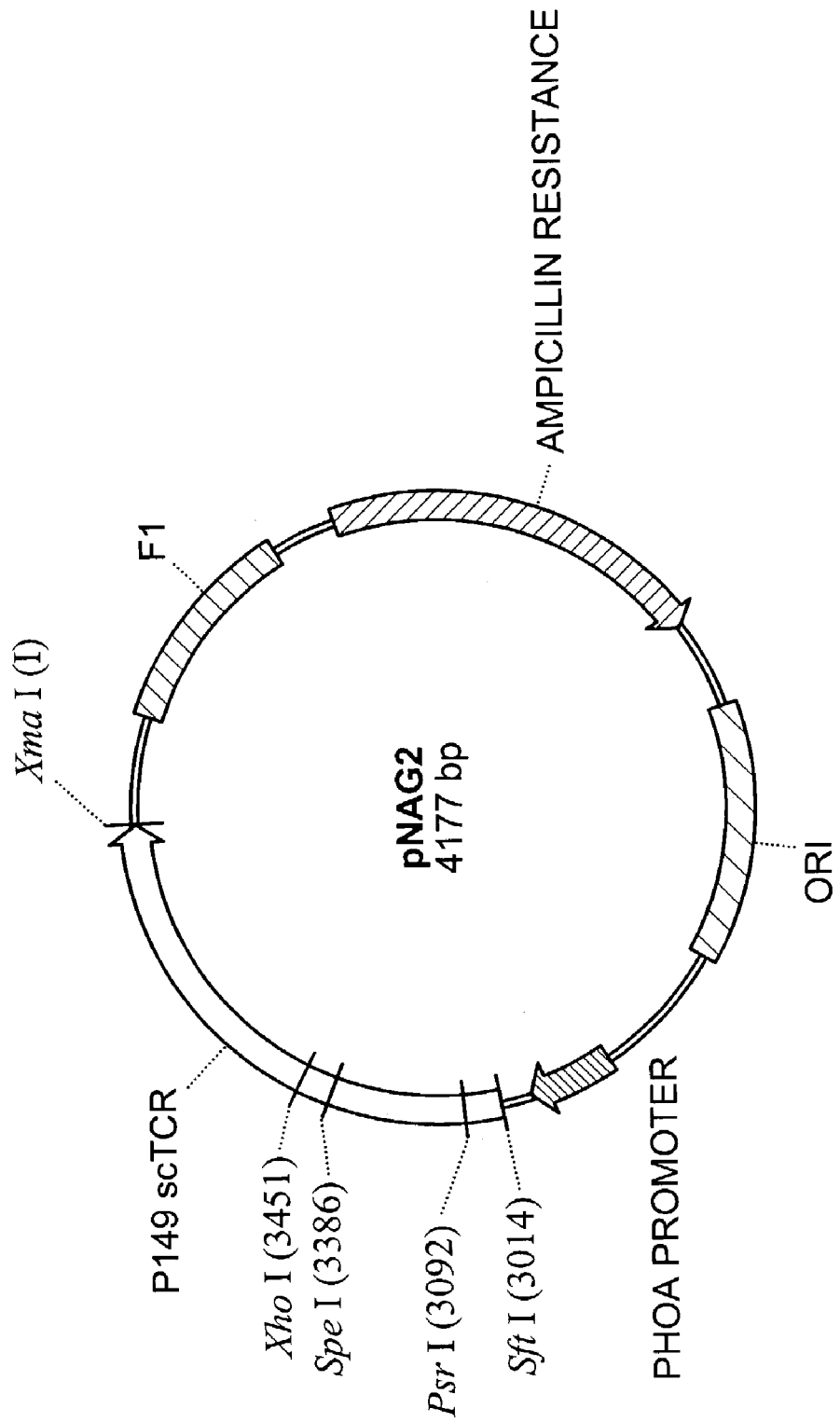
FIG. 1 is a schematic illustration of the pNAG2 vector.

As summarized above, we have isolated a highly useful T-cell receptor (TCR) heterodimer that generally includes a Vα chain and a Vβ chain i.e., a two-chain complex. More preferred heterodimers bind, typically in the context of an HLA-A2.1 MHC molecule, amino acid sequence between from about 264 to about 272 of the human p53 protein sequence, preferably spanning amino acid positions 264 to 272 of that protein i.e., the following "target" amino acid sequence: Leu Leu Gly Arg Asn Ser Phe Glu Val (SEQ ID NO. 1). As also summarized previously, good binding is determined by a standard T-cell binding assay provided below.

The general structure of many naturally-occurring TCR heterodimers has been reported. See, e.g., Davis *Ann. Rev. of Immunology* 3: 537 (1985); *Fundamental Immunology* 3rd Ed., W. Paul Ed. Raven Press LTD. New York (1993) and references disclosed therein.

In general, a T cell recognizes antigen presented on the surfaces of cells by means of the T cell receptors expressed on their cell surface. TCRs are disulfide-linked heterodimers, most consisting of α and β chain glycoproteins. T cells use mechanisms to generate diversity in their receptor molecules similar to those mechanisms for generating antibody diversity operating in B cells (Janeway and Travers; Immunobiology 1997). Similar to the immunoglobulin genes, TCR genes are composed of segments that rearrange during development of T cells. TCR polypeptides consist of amino terminal variable and carboxy terminal constant regions. While the carboxy terminal region functions as a transmembrane anchor and participates in intracellular signaling when the receptor is occupied, the variable region is responsible for recognition of antigens. The TCR α chain contains variable regions encoded by V and D segments only, while the β chain contains additional joining (J) segments. The rearrangement of these segments in a diverse repertoire of TCRs capable of recognizing an incredibly large number of different antigens displayed in the context of different MHC molecules.

There have been reports of specific TCRs which recognize particular antigens. For example, the pending U.S. patent applications U.S. Ser. No. 08/813,781 and U.S. Ser. No. 09/422,375, incorporated herein by reference; and International publications PCT/US98/04274 and PCT/US99/24645, and references discussed therein disclose methods of preparing and using specific TCRs. Additionally, particular specific TCRs have been produced by recombinant methods as soluble, single-chain TCRs (sc-TCR). Methods for production and use of sc-TCRs have been disclosed and are described in pending U.S. patent application Ser. No. 08/943, 086, and International application PCT/US98/20263 which are incorporated herein by reference.

Preferred TCR heterodimers of the invention include an α chain and a β chain covalently linked together by virtue of at least one disulfide bond. Non-covalent binding, e.g., hydrogen bonding, between the chains has been reported. Each of the chains can be between from about 150 to about 350 amino acids long, preferably between from about 200 to about 300 amino acids long, more preferably between from about 250 to about 290 amino acids long, with about 280 amino acids being useful for most invention applications. Heterodimeric TCR molecules according to the invention are optionally glycosylated.

By the phrase "HLA-A2.1 MHC molecule" is meant a primate class I MHC molecule, preferably a human molecule, that is capable of generating or of being recognized by A2.1 restricted, tumor-reactive cytotoxic T lymphocytes (CTLs) bearing TCRs specific for peptides having sequence obtained from human p53 protein. A preferred amino acid sequence is usually between from about amino acid 250 to about amino acid 290 of the human p53 sequence, preferably between from about amino acid 264 to about amino acid 272 of that sequence, with sequence spanning positions amino acid 264 to amino acid 272 of the p53 protein being preferred for most applications.

More preferred HLA-A2.1 MHC molecules in accord with the invention are integral membrane proteins that often include a glycoprotein heavy chain having three extracellular domains (i.e. α1, α2 and α3), a transmembrane domain and a cytoplasmic domain. The heavy chain is typically non-covalently associated with a soluble subunit β2-microglobulin. The α1 and α2 domains of the heavy chain fold together to form the peptide-binding groove for a particular p53 sequence. The association between the heavy chain and 132-microglobulin may help stabilize the peptide-binding groove. The MHC molecule may consist of nearly any combination of a naturally occurring or recombinant class I heavy chain (or fragments thereof) and a naturally occurring or recombinant β2-microglobulin molecule (or biologically active fragments thereof).

Information relating to the human p53 amino acid and nucleic acid sequence is available from the National Center for Biotechnology Information (NCBI)— Genetic Sequence Data Bank (Genbank) at the National Library of Medicine, 38A, 8NO5, Rockville Pike, Bethesda, Md. 20894. Genbank is also available on the internet at http://www.ncbi.nlm.nih.gov. See, Benson, D. A. et. al. (1997) *Nucl. Acids. Res.* 25: 1 for a description of Genbank. See also Theobald, M et. al. (1995), supra (disclosing also the p53 amino acid numbering scheme adopted in this application).

It has been reported that expression of the tumor suppressor protein p53 is upregulated on malignant cells. It has also been shown that 50% of all tumors express increased levels of p53 on their surface (Holliston, M. D., et. al., *Science* (1991), 253: 49).

Information relating to making and using the human HLA-A2.1 MHC molecule, particularly in the context of tumor cells expressing p53 has been reported by Theobald, M et. al. (1995), supra, including references disclosed therein. See also PCT/US97/03611 and U.S. Ser. No. 08/812,393 filed on Mar. 5, 1997, which applications claim the benefit of U.S. Ser. No. 60/012,845 filed on Mar. 5, 1996. The disclosures of said PCT/US97/03611, U.S. Ser. No. 08/812,393, and U.S. Ser. No. 60/012,845 applications are hereby incorporated by reference.

Methods for detecting productive binding between the HLA-A2.1 MHC molecule and an amino acid sequence obtained from the p53 protein sequence have been reported, e.g., by Theobald, M et. al. (1995), supra. In general, the methods involve using recognized competition assays to assess binding of p53 peptide to the HLA-A2.1 molecule. See, also, the PCT/US97/03611, U.S. Ser. No. 08/812,393, and U.S. Ser. No. 60/012,845 applications.

More particular heterodimeric TCR molecules in accord with the invention include a Vα chain that is at least about 90% identical to the Va3 chain shown in FIGS. 4A-C below, preferably between from about 95% to about 100% identical. Additional heterodimers of the invention include a Vβ chain that is at least about 90% identical to the Vb3 chain shown in FIGS. 4A-C (SEQ ID NO. 2), preferably between from about 95% to about 100% identical.

Preferably, to determine the percent identity of two amino acid sequences, the sequences are aligned for optimal comparison purposes (e.g., gaps are introduced in one or both of a first and a second amino acid for optimal alignment and non-homologous sequences are disregarded for comparison purposes). A "comparison window" refers to a segment of any one of the number of contiguous positions selected from the group consisting of from 25 to 600, usually about 50 to about 200, more usually about 100 to about 150 in which a sequence may be compared to a reference sequence of the same number of contiguous positions after the two sequences are optimally aligned. To identify sequences with the appropriate % identity as disclosed herein, the comparison window may comprise any of the segment ranges described above.

The percent identity between the two sequences is a function of the number of identical positions shared by the sequences, taking into account the number of gaps, and the length of each gap which need to be introduced for optimal alignment of the two sequences. The amino acid residues at corresponding amino acid positions are then compared. When a position in the first sequence is occupied by the same amino acid residue as the corresponding position in the second sequence, then the molecules are identical at that position (as used herein amino acid "identity" is equivalent to amino acid "homology").

Percent identity between two sequences can be determined using a mathematical algorithm as is known in the art (see, e.g., Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991). For example, the percent identity between two amino acid sequences can be determined using the Needleman and Wunsch algorithm (J. Mol. Biol. (48): 444-453, 1970) which is part of the GAP program in the GCG software package (available at http://www.gcg.com), by the local homology algorithm of Smith & Waterman (Adv. Appl. Math. 2: 482, 1981), by the search for similarity methods of Pearson & Lipman (Proc. Natl. Acad. Sci. USA 85: 2444, 1988) and Altschul, et. al. (Nucleic Acids Res. 25(17): 3389-3402, 1997), by computerized implementations of these algorithms (GAP, BESTFIT, FASTA, and BLAST in the Wisconsin Genetics Software Package (available from, Genetics Computer Group, 575 Science Dr., Madison, Wis.), or by manual alignment and visual inspection (see, e.g., Ausubel et. al., supra).

Gap parameters can be modified to suit a user's needs. For example, when employing the GCG software package, a NWSgapdna.CMP matrix and a gap weight of 40, 50, 60, 70, or 80 and a length weight of 1, 2, 3, 4, 5, or 6 can be used. Exemplary gap weights using a Blossom 62 matrix or a PAM250 matrix, can be 16, 14, 12, 10, 8, 6, or 4, while exemplary length weights can be 1, 2, 3, 4, 5, or 6. The percent identity between two amino acid also can be determined using the algorithm of E. Myers and W. Miller (CABIOS 4: 11-17, 1989) which has been incorporated into the ALIGN program (version 2.0), using a PAM120 weight residue table, a gap length penalty of 12 and a gap penalty of 4.

Thus, by the term "100% identical" is meant that the amino acids of a subject V chain are 100% homologous to the corresponding naturally-occurring TCR Vβ or Vα chain or allelic variants thereof with the same binding characteristics (e.g., no significant difference in binding specificity and affinity]. That is, the subject V chain has the same length and amino sequence of the corresponding and naturally-occurring chain or allelic variants thereof with the same binding characteristics.

Additionally preferred heterodimeric molecules of the invention include a Cα and Cβ sequence having at least about 90% identity to the Cα and Cβ chains sequences shown in FIGS. 5 [SEQ ID NO. 3] and 4A-C (SEQ ID NO. 2), respectively. Preferably, the Cα and Cβ sequences are between from about 95% to about 100% identical to the Cα and Cβ chains sequences shown in FIGS. 5 and 4A-C.

The general structure of sc-TCR molecules and methods of making and using same have been disclosed in the pending U.S. Ser. No. 08/813,781 and PCT/US98/04274. The disclosures of said U.S. Ser. No. 08/813,781 and PCT/US98/04274 are hereby incorporated by reference.

See also the pending U.S. Ser. No. 08/943,086 and PCT/US98/20263 for additional disclosure relating to making and using sc-TCR molecules. The disclosures of said U.S. Ser. No. 08/943,086 and PCT/US98/20263 applications are hereby incorporated by reference.

As provided above, the present invention features highly useful single-chain T cell receptor (sc-TCR) proteins that generally include between from about one to about five Vβ chains covalently linked to between from about one to five VP chains by between from about one to five peptide linker sequences. Preferred sc-TCR include about one Vα chain and about one VP chain linked together by about one peptide linker sequence as provided herein.

Additionally preferred sc-TCRs are typically capable of binding, in the context of the HLA-A2.1 MHC molecule, peptides having sequence obtained from human p53 protein. A preferred amino acid sequence is usually between from about amino acid 250 to about amino acid 290 of the human p53 sequence, preferably between from about amino acid 264 to about amino acid 272 of that sequence, with sequence spanning amino acid positions 264 to 272 of the p53 protein being preferred for most applications. Good binding is preferably determined by the standard T cell receptor (TCR) ELISA assay described below.

More specific sc-TCR molecules in accord with the invention include a Vα chain that is at least about 90% identical to the Va3 chain shown in FIGS. 4A-C (SEQ ID NO. 2) below, preferably between from about 95% to about 100% identical. Additionally preferred sc-TCR molecules include a Vβ chain that is at least about 90% identical to the Vb3 chain shown in FIGS. 4A-C (SEQ ID NO. 2), preferably between from about 95% to about 100% identical.

Additionally preferred sc-TCR molecules of the invention include a Cβ sequence having at least about 90% identity to the Cβ chain sequence shown in FIGS. 4A-C. Preferably, the Cβ sequence is between from about 95% to about 100% identical to the Cβ chain sequence shown in FIGS. 4A-C.

It has been discovered that the Cα chain is not always required to demonstrate good sc-TCR binding in the standard T cell receptor (TCR) ELISA assay. In these embodiments, it is not necessary to include the Cα chain as part of the sc-TCR molecule. For example, see FIGS. 4A-5C below (disclosing especially preferred 264 sc-TCR sequences). However, sc-TCR molecules may include at least one Cα chain (as shown in FIG. 5, for example) or a functional fragment thereof, preferably between from about one to five of such chains, with about one of such a Cα chain being suitable.

In invention embodiments in which a particular sc-TCR includes the Cα chain or a functional fragment thereof, that chain will preferably bear at least about 90% identity to the Cα chain sequence shown in FIG. 5 (SEQ ID NO. 3). Preferably, that sequence is between from about 95% to about 100% identical to the Cα chain sequence shown in FIG. 5 (SEQ ID NO. 3).

More particular sc-TCR molecules in line with the invention include those having covalently linked in sequence: 1) a Vα3 chain as shown in FIGS. 4A-C (SEQ ID NO. 2); 2) a peptide linker; and 3) a Vβ3 chain as shown in FIGS. 4A-C (SEQ ID NO. 2). In one embodiment, the sc-TCR molecule further includes a Cβ chain as provided in FIGS. 4A-C (SEQ ID NO. 2) preferably linked to the C-terminus of the Vβ3 chain.

In an embodiment of the foregoing specific sc-TCR molecule, the sc-TCR further includes the Cα chain as provided in FIG. 5 (SEQ ID NO. 3), the chain preferably being covalently linked between the C-terminus of the Vα chain and the N-terminus of a peptide linker.

Typical Vα and Vβ chains of the heterodimeric and single chain TCR molecules disclosed herein are generally about 200 to 400 amino acids in length, preferably about 300 to 350 amino acids in length. Methods for determining amino acid length are known in the field and include polyacrylamide gel electrophoresis.

As discussed, preferred sc-TCR molecules of the invention include one or more peptide linker sequences preferably positioned between the VcL and Vβ chains. Preferably the linker sequence comprises from about 7 to 20 amino acids, more preferably from about 8 to 16 amino acids. The linker sequence is preferably flexible so as not hold sequence derived from the human p53 protein (and presented in the context of the HLA-A2.1 molecule) in a single desired conformation. Specifically, the peptide linker sequence can be positioned between the TCR variable chains typically to enhance binding flexibility between those chains. The linker predominantly comprises amino acids with small side chains, such as glycine, alanine and serine, to provide for flexibility. Preferably about 80 or 90 percent or greater of the linker sequence comprises glycine, alanine or serine residues, particularly glycine and serine residues. For heterodimeric TCRs, the linker sequence is suitably linked to the β chain of the TCR molecule, although the linker sequence also could be attached to the α chain of the TCR molecule. Alternatively, the linker sequence may be linked to both α and β chains of the TCR molecule.

See the following references for supplemental disclosure relating to making and using sc-TCR molecules: Novotny, J. et. al. *PNAS* (USA) 88: 8646 (1991); Soo Hoo, W. F. et. al. *PNAS* (USA) 89: 4759 (1992); Wülfing, C. and Plückthun, A., *J. Mol. Biol.* 242: 655 (1994); Kurucz, I. et. al. *PNAS* (USA) 90: 3830 (1993); PCT WO 96/13593; Ward, E. S. et. al., *J. Mol. Biol.* 224: 885, (1992); Schlueter, C. J. et. al. *J. Mol. Biol.* 256: 859 (1996); Mariuzza, R. A. and Winter, G., (1989) 264:7310; Gascoigne, N. R. J., et. al., *PNAS* (USA) (1987), 84: 2936.

In a particular invention embodiment, a suitable linker sequence is ASGGGGSGGG (i.e., Ala Ser Gly Gly Gly Gly Ser Gly Gly Gly) (SEQ ID NO. 4] repeated as many as four or more times, preferably linked to the first amino acid of the β domain of the TCR. Different linker sequences could be used including any of a number of flexible linker designs that have been used successfully to join antibody variable regions together, see Whitlow, M. et al., (1991) *Methods: A Companion to Methods in Enzymology* 2:97-105. Suitable linker sequences can be readily identified empirically. Additionally, suitable size and sequences of linker sequences also can be determined by conventional computer modeling techniques based on the predicted size and shape of the TCR molecule.

Accordingly, and in one embodiment, the invention features particular sc-TCR molecules in which at least one of the peptide sequences, preferably one of same has the following sequence: Gly Gly Gly Gly Ser (SEQ ID NO. 5) repeated as many as four or more times.

See also the co-pending application entitled T-cell Receptor Fusions and Conjugates and Methods of Use Thereof filed on Jun. 5, 2001 (U.S. Ser. No. 09/874,907 by inventors Jon A. Weidanz, Kimberlyn F. Card, and Hing C. Wong) for additional information relating to particular 264 TCR related molecules; the disclosure of said co-pending application is hereby incorporated by reference.

In some settings it can be useful to make the sc-TCR molecules of the present invention polyvalent, e.g., to increase the valency of the sc-TCR. Briefly stated, the polyvalent TCR protein is made by covalently linking together between two and four proteins (the same or different) by using e.g., standard biotin-streptavidin labeling techniques, or by conjugation to suitable solid supports such as latex beads. Chemically cross-linked proteins (for example cross-linked to dendrimers) are also suitable polyvalent species. For example, the protein can be modified by including sequences encoding amino acid residues with chemically reactive side chains such as Cys or His. Such amino acids with chemically reactive side chains may be positioned in a variety of positions in the linked protein, preferably distal to the antigen-binding region of the TCR. For example, the C-terminus of a Cβ chain fragment of a soluble protein can be covalently linked to a protein purification tag or other protein which includes such a reactive amino acid(s). Suitable side chains can be included to chemically link two or more proteins to a suitable dendrimer particle to give a multivalent molecule. Dendrimers are synthetic chemical polymers that can have any one of a number of different functional groups of their surface (D. Tomalia, *Aldnchimica Acta,* 26:91-101 (1993)). Exemplary dendrimers for use in accordance with the present invention include, e.g., E9 starburst polyamine dendrimer and E9 combust polyamine dendrimer, which can link cysteine residues.

Successful presentation of a human p53 sequence as provided herein to a TCR molecule of the invention can be determined by a variety of specified assays, including the T cell binding assays and TCR ELISA discussed below. Alternatively, successful presentation can be detected and quantified if desired by monitoring the activity of a T cell by following either induction of or inhibition of T cell proliferation, or initiation or inhibition of an immune response to a particular site or target. Such suitable assays include, but are not limited to, in vitro assays that include sequential steps of culturing T cells to proliferate same, and contacting the T cells with a MHC-peptide antigen complex and then evaluating biological response by the cells. See the U.S. Ser. No. 08/813,781 and PCT/US98/04274 applications for more specific examples of such assays.

In one aspect, the functionality of a TCR molecule is determined by monitoring the ability of the TCR to recognize the appropriate p53 peptide in the context of an appropriate MHC molecule (e.g., HLA-2A), e.g., by monitoring binding of the TCR to MHC:p53 peptide complexes. Such complexes can be presented on a cell, in which case TCR functionality is measured by contacting a labeled TCR with a p53 presenting cell and measuring binding to the cell as compared to binding to a non-p53 presenting cell. Labeled cells can be detected microscopically or by using flow cytometry assays as are routine in the art.

In another aspect, a non-cell based assay is used, such as a TCR Enzyme Linked Immunosorbant Assay (ELISA). For example, the TCR can be bound directly to a support and its ability to bind to MHC:p53 peptide complexes can be measured, or the MHC:p53 complex can be bound to the support and the ability of the complex to bind to the TCR can be measured. Suitable supports include, but are not limited to, wells of a microtiter plate, cell culture plates, membrane, glass or polymer substrates, and the like. Instead of direct binding of the TCR to the support, the support can be coated with an antibody that recognizes the TCR such that the bound antibody can capture and thereby indirectly bind the TCR to the support. Suitable controls for such assays will be obvious to those of skill in the art, and include, but are not limited to, MHC molecules bound to irrelevant antigens, non-p53 recognizing TCR's, buffer, etc. In a TCR ELISA, either the TCR molecule or the MHC or peptide can be labeled. Preferably, the molecule bound to the support is unlabeled. As used herein, "labeled" refers to direct or indirect labeling. Thus, a "labeled TCR molecule" may comprise a label directly linked to it or may comprise a TCR bound indirectly or directly by a labeled binding partner, such as an antibody, which recognizes the TCR or which recognizes an antibody bound to the TCR. As used herein, "linked" refers to a stable association between two molecules which can be covalent or non-covalent.

Assays to monitor TCR functionality may also include assays to measure TCR-mediated signal transduction. In one aspect, a nucleic acid construct encoding a TCR heterodimer is introduced into a cell which does not express a TCR or at least does not express a TCR of the same specificity. The ability of the TCR-expressing cell to transduce the appropriate signals upon binding to a p53:MHC complex can then be monitored. For example, the ability of the TCR-expressing cell to produce IL-2 may be measured. sc-TCRs also may be transfected into cells. In such assays, the sc-TCR is preferably expressed as a fusion with a transmembrane domain polypeptide (e.g., from an immunoglobulin molecule) and more preferably, also as a fusion with an appropriate cytoplasmic signaling domain. In one aspect, the cytoplasmic signaling domain is a CD3 zeta molecule. MHC:p53 complexes may be presented by natural or engineered antigen presenting cells or may be isolated complexes.

The ability of a TCR to mediate a cytolytic response also can be determined. For such an assay, a nucleic acid construct encoding a TCR molecule preferably is introduced into a cell which can express appropriate co-stimulatory molecules.

In all of the above assays, a "functional" TCR is one which demonstrates increased function (e.g., increased binding, increased signal transduction, such as IL-2 production, increased cell killing, and the like] as compared to a control TCR which does not bind to an MHC:p53 complex. The amount of increased function necessary to demonstrate a "functional TCR" will necessarily depend on the type of assay used. For example, in one aspect, an assay value which indicates a functional TCR is about 10% greater, about 15% greater, about 20% greater, about 30% greater, about 40% greater, about 50% greater, about 60% greater, about 70% greater, about 80% greater, about 90% greater or about 100% greater than a value obtained for a control TCR. In other assays, an assay value which indicates a functional TCR is about 2-fold greater, about 4-fold greater, about 8 fold greater, about 10-fold greater, about 20-fold greater, about 30-fold greater, about 40-fold greater, about 50-fold greater, about 60-fold greater, about 70-fold greater, about 80-fold greater, about 90-fold greater, or about 100-fold greater than a value obtained for a control TCR. For other assays, an assay value which indicates a functional TCR is one which is statistically significantly different from a value obtained from a control assay with $p<0.05$. One of skill in the art can routinely evaluate measures of significance for particular assays used.

In general, preparation of the TCR of the invention can be accomplished by procedures disclosed herein and by recognized recombinant DNA techniques involving, e.g., polymerase chain amplification reactions (PCR), preparation of plasmid DNA, cleavage of DNA with restriction enzymes, preparation of oligonucleotides, ligation of DNA, isolation of mRNA, introduction of the DNA into a suitable cell, transformation or transfection of a host, culturing of the host. Additionally, the TCR molecules can be isolated and purified using chaotropic agents and well known electrophoretic, centrifugation and chromatographic methods. See generally, Sambrook et. al., *Molecular Cloning: A Laboratory Manual* (2nd ed. (1989); and Ausubel et. al., *Current Protocols in Molecular Biology*, John Wiley & Sons, New York (1989) for disclosure relating to these methods.

See also the U.S. Ser. No. 08/813,781 and PCT/US98/04274 and the co-pending application referenced above entitled T-cell Receptor Fusions and Conjugates and Methods of Use Thereof filed on Jun. 5, 2001 (U.S. Ser. No. 09/874,907 by inventors Jon A. Weidanz, Kimberlyn F. Card, and Hing C. Wong) for more specific background information relating to making and using the molecules disclosed herein.

As discussed, preferred molecules in accord with the invention demonstrate good binding in what is referred to herein as a standard T cell binding assay or TCR ELISA. By the phrase "standard T cell binding assay" is meant a binding test that detects and preferably quantitates binding between a suitable T cell and an MHC molecule complexed with an antigen. Briefly stated, a preferred test involves providing a detectably labeled MHC molecule, contacting the labeled MHC molecule (complexed with the antigen) and the T cell under conditions conducive to forming an MHC-antigen:T cell complex and monitoring formation of that complex using standard detection methods. Formation of the complex can be quantified if desired. Other assays for TCR function as described above may also be used.

Preferred TCR molecules including the heterodimers and single chain molecules provided herein are generally of sufficient size to allow for specific binding of the TCR to the MHC molecule. In embodiments where the MHC is complexed with an antigen also referred to as a peptide-MHC molecule, the TCR molecules contain at least the CDR binding loops forming the MHC-peptide binding pocket. Useful α/β TCR molecules containing an MHC-peptide binding pocket preferably consists of at least the α chain variable domain (about amino acid 1 to about amino acid 110 to about amino acid 130 dependent on CDR length of the α chain) and the β chain variable domain (about amino acid 1 to about amino acid 110 to about amino acid 130 dependent on CDR length of the β chain).

More preferred TCR molecules for use in accord with this invention exhibit significant binding activity in what has been referred to herein as the standard T-cell binding test. Preferably, the TCR molecule specifically binds its cognate MHC antigen molecule complex at a level which is significantly different from binding to an irrelevant (control) TCR (where "significance" is determined using routine statistical methods known in the art, e.g., with $p \leq 0.05$). Preferably, binding is at least about 2-fold, at least about 10-fold, at least-about 20-fold, at least about 50-fold, or at least about 100-fold higher than control values. Examples of suitable control molecules include a 149 TCR molecule as provided, e.g., in U.S. Ser. No. 08/813,781; U.S. Ser. No. 09/422,375; PCT/US98/04274; PCT/US99/24645; as well as other references cited herein.

Highly useful in vitro and in vivo T cell binding assays have been disclosed in published PCT Application Nos. PCT/US95/09816, PCT/US96/04314 and PCT/US97/01617, as well as the pending U.S. patent application Ser. Nos. 08/382,454, 08/596,387 and 08/943,086. The disclosed T cell binding assays can be used or readily adapted if necessary to identify good binding between TCR molecules of this invention and the disclosed p53 amino acid sequence displayed in the context of an appropriate MHC molecule. The disclosures of said published PCT application Nos. PCT/US95/09816, PCT/US96/04314, PCT/US97/01617, and pending U.S. application Ser. Nos. 08/382,454, 08/596,387 are each incorporated herein by reference.

A preferred example of the standard T cell binding test has been disclosed in a co-pending application filed on May 16, 2001 entitled Modulation of T-cell Receptor Interactions (U.S. Ser. No. 09/859,012 by inventors Peter Rhode, Vaughan Wittman, Jon A. Weidanz, Martin Burkhardt, Kimberlyn F. Card, Rony Tal, Jorge Acevedo, and Hing C. Wong), the disclosure of which co-pending application is hereby incorporated by reference (hereinafter "co-pending application filed on May 16, 2001"). The foregoing co-pending application filed on May 16, 2001 is a continuation-in-part of U.S. Ser. No. 60/206,920. The disclosure of the U.S. Ser. No. 60/206,920 application is incorporated herein by reference.

In particular, Example 15 of the co-pending application filed on May 16, 2001 discloses an illustration of the standard T cell binding test. Typically, the test involves producing T cells that express the subject TCR of interest, e.g., a heterodimer in accord with the invention; and then staining those cells with a suitable class I MHC molecule, particularly the HLA-A2.1 molecule. Methods for staining the T cells involving conventional biotin/streptavidin technologies have been disclosed in the co-pending application filed on May 16, 2001. As disclosed, a preferred detection format is flow cytometry although other detection strategies may be more preferred for some applications.

By the phrase "standard T cell receptor (TCR) ELISA" is meant to include, but is not limited to, any one of the suitable assays disclosed, e.g., in the foregoing co-pending application filed on May 16, 2001. A preferred assay involves manipulating single chain or heterodimeric TCR constructs using, e.g., a plate-based ELISA. Briefly stated, the assay involves detectably labeling the single-chain or heterodimeric TCR, contacting the labeled TCR molecule with a suitable peptide-loaded MHC molecule, preferably the HLA-A2.1 molecule disclosed herein, in which the contacting is under conditions sufficient to form a TCR:MHC-peptide complex. Preferred labeling strategies are disclosed throughout the co-pending application filed on May 16, 2001 and include standard biotin/streptavidin labeling strategies. See, for instance, Example 15 of the co-pending application filed on May 16, 2001.

As discussed, preferred TCR molecules of the invention bind, typically in the context of an HLA-A2.1 MHC molecule, amino acid sequence between from about amino acid 264 to about amino acid 272 of the human p53 protein sequence, preferably spanning amino acid positions 264 to 272 of that protein, i.e., the following "target" amino acid sequence: Leu Leu Gly Arg Asn Ser Phe Glu Val (SEQ ID NO. 1). Additionally contemplated are derivatives of the target amino acid, i.e., amino acid sequences having at least one conservative amino acid substitution therein. In embodiments in which two or more conservative amino acids are substituted for any of the target sequence residues, those substitutions can be adjacent or non-adjacent as needed.

Preferably, conservative substitutions are amino acid substitutions that are phenotypically silent, i.e., the substitutions do not significantly affect the binding of the TCR in a standard assays. An example of a conservative amino acid substituted for another amino acid is a tyrosine amino acid substituted for the phenylalanine at amino acid position 7 (amino acid position 270 with respect to human p53 protein) of the preferred target sequence. In contrast, an arginine substituted for any of the leucine residues in the target sequence would be an example of a non-conservative amino acid substitution. Preferred examples of conservative amino acid replacements have been disclosed in the U.S. Pat. No. 6,127,524 (FIGS. 15A-B); the disclosure of which is incorporated herein by reference.

The invention further provides nucleic acid sequences (DNA or RNA) and particularly DNA sequences that encode the present TCR molecules including preferred heterodimers and single chain constructs. Such DNA sequences are preferably carried by a vector suited for extrachromosomal replication such as a phage, virus, plasmid, phagemid, cosmid, YAC, or episome. In some embodiments, the DNA vector can encode another helper protein whose sole function is to facilitate preparative methods described herein and to obtain significant quantities of the protein. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.) or transfected with an expression vector; insect cell systems infected with virus (e.g., baculovirus); microorganisms such as yeast containing yeast vectors, or bacteria transformed with bacteriophage DNA, plasmid DNA or cosmid DNA. Depending on the host-vector system utilized, any one of a number of suitable transcription and translation elements may be used. See generally Sambrook et. al., supra and Ausubel et. al. supra.

In general, a preferred DNA vector according to the invention comprises a nucleotide sequence linked by phosphodiester bonds comprising, in a 5' to 3' direction a first cloning site for introduction of a first nucleotide sequence encoding a TCR chain, operatively linked to a sequence encoding an effector molecule, i.e. a fusion protein or conjugate.

As used herein, an "effector molecule" refers to an amino acid sequence such as a protein, polypeptide or peptide; a sugar or polysaccharide; a lipid or a glycolipid, glycoprotein, lipoprotein or chemical agent that can produce the desired effects as discussed herein. Thus, suitable molecules include regulatory factors, enzymes, antibodies, or drugs as well as DNA, RNA, and oligonucleotides. The biologically active or effector molecule can be naturally-occurring or it can be synthesized from known components, e.g., by recombinant or chemical synthesis and can include heterologous components. A biologically active or effector molecule is generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis. Desired effects of the invention include, for example, either to induce cell proliferation or cell death, initiate an immune response or to act as a detection molecule for diagnostic purposes as determined by the assays disclosed below, including an assay that includes sequential steps of culturing cells to proliferate same, and contacting the cells with a TCR fusion complex of the invention and then evaluating whether the TCR fusion complex inhibits further development of the cells.

In most instances, it will be preferred that each of the fusion protein components encoded by the DNA vector be provided in a "cassette" format. By the term "cassette" is meant that each component can be readily substituted for another component by standard recombinant methods. To make the vector coding for the TCR molecules provided herein, the sequence coding for the TCR molecule is linked to a vector sequence by use of suitable ligases.

If desired, other nucleotide sequences can be included in the gene construct. For example, a promoter sequence, which controls expression of the sequence coding for the TCR molecule, or a leader sequence, which directs the TCR fusion complex to the cell surface or the culture medium, can be included in the construct or be present in the expression vector into which the construct is inserted. An immunoglobulin or CMV promoter is particularly preferred for mammalian cell expression.

It is emphasized that components of the TCR molecules of this invention, including, but not limited to, variable chains, transmembrane domains, constant chains, etc., can be organized in nearly any order provided each is capable of performing its intended function.

A number of strategies can be employed to express TCR molecules provided herein. For example, the sc-TCR molecule binding the target amino acid sequence of SEQ ID NO: 1 in the context of an HLA molecule can be incorporated into a suitable vector by known means such as by use of restriction enzymes to make cuts in the vector for insertion of the construct followed by ligation. The vector containing the recombinant gene construct is then introduced into a suitable host for expression of the TCR fusion peptide. See, generally, Sambrook et. al., supra. Selection of suitable vectors can be made empirically based on factors relating to the cloning protocol. For example, the vector should be compatible with, and have the proper replicon for, the host that is being employed. Further, the vector must be able to accommodate the DNA sequence coding for the TCR molecule that is to be expressed. Suitable host cells include eukaryotic and prokaryotic cells, preferably those cells that can be easily transformed and exhibit rapid growth in culture medium. Specifically preferred host cells include prokaryotes such as *E. coli, Bacillus subtillus*, etc. and eukaryotes such as animal cells and yeast strains, e.g., *S. cerevisiae*. Mammalian cells are generally preferred, particularly J558, NSO, SP2-O or CHO. Other suitable hosts include, e.g., insect cells such as Sf9. Conventional culturing conditions are employed. See Sambrook, supra. Stable transformed or transfected cell lines can then be selected. Cells expressing a TCR molecule can be determined by known procedures. For example, expression of a TCR molecule, preferably a heterodimer linked to an immunoglobulin can be determined by an ELISA specific for the linked immunoglobulin and/or by immunoblotting.

As mentioned generally above, a host cell can be used for preparative purposes to propagate nucleic acid encoding a desired fusion protein. Thus, a host cell can include a prokaryotic or eukaryotic cell in which production of the fusion protein is specifically intended. Thus, host cells specifically include bacterial, yeast, fly, worm, plant, frog, mammalian cells and organs that are capable of propagating nucleic acid encoding the fusion. Non-limiting examples of mammalian cell lines which can be used include CHO dhfr-cells (Urlaub and Chasm, *Proc. Natl. Acad. Sci. USA*, 77:4216 (1980)), 293 cells (Graham et. al., *J Gen. Virol.*, 36:59 (1977)) or myeloma cells like SP2 or NSO (Galfre and Milstein, *Meth. Enzymol.*, 73(B):3 (1981)).

Host cells capable of propagating nucleic acid encoding a desired heterodimer or single chain TCR encompass non-mammalian eukaryotic cells as well, including insect (e.g., *Sp. frugiperda*), yeast (e.g., *S. cerevisiae, S. pombe, P. pas-*

*toris., K. lactis, H. polymorpha*; as generally reviewed by Fleer, R., *Current Opinion in Biotechnology*, 3(5):486-496 (1992)), fungal and plant cells. Also contemplated are certain prokaryotes such as *E. coli* and *Bacillus*.

Nucleic acid encoding a desired fusion protein can be introduced into a host cell by standard techniques for transfecting cells. The term "transfecting" or "transfection" is intended to encompass all conventional techniques for introducing nucleic acid into host cells, including calcium phosphate co-precipitation, DEAE-dextran-mediated transfection, lipofection, electroporation, microinjection, viral transduction and/or integration. Suitable methods for transfecting host cells can be found in Sambrook et. al. supra, and other laboratory textbooks.

The present invention further provides a production process for isolating any one of the TCR molecules disclosed herein. In the process, a host cell (e.g., a yeast, fungus, insect, bacterial or animal cell), into which has been introduced a nucleic acid encoding the protein of interest operatively linked to a regulatory sequence, is grown at production scale in a culture medium to stimulate transcription of the nucleotide sequence encoding the fusion protein of interest. Subsequently, the TCR molecule is isolated from harvested host cells or from the culture medium. Standard protein purification techniques can be used to isolate the protein of interest from the medium or from the harvested cells. In particular, the purification techniques can be used to express and purify a desired TCR protein on a large-scale (i.e., in at least milligram quantities) from a variety of implementations including roller bottles, spinner flasks, tissue culture plates, bioreactors, or fermentors.

An expressed TCR molecule according to the invention can be isolated and purified by known methods. Typically the culture medium is centrifuged and then the supernatant is purified by affinity or immunoaffinity chromatography, e.g., Protein-A or Protein-G affinity chromatography or an immunoaffinity protocol comprising use of monoclonal antibodies that bind the expressed TCR molecule. Such molecules can be separated and purified by appropriate combination of known techniques. These methods include, for example, methods utilizing solubility such as salt precipitation and solvent precipitation, methods utilizing the difference in molecular weight such as dialysis, ultra-filtration, gel-filtration, and SDS-polyacrylamide gel electrophoresis, methods utilizing a difference in electrical charge such as ion-exchange column chromatography, methods utilizing specific affinity such as affinity chromatography, methods utilizing a difference in hydrophobicity such as reverse-phase high performance liquid chromatography, and methods utilizing a difference in isoelectric point such as isoelectric focusing electrophoresis and metal affinity columns such as Ni-NTA. See, generally, Sambrook et. al. and Ausubel et. al. supra for disclosure relating to these methods.

It is preferred that particularly the single chain TCR molecules of the present invention be substantially pure. That is, the molecules have been isolated from cell substituents that naturally accompany it so that the fusion proteins are present preferably in at least 80% or 90% to 95% homogeneity (w/w). Such proteins having at least 98 to 99% homogeneity (w/w) are most preferred for many pharmaceutical, clinical and research applications. Once substantially purified, the protein should be substantially free of contaminants for therapeutic applications. Once purified partially or to substantial purity, the soluble TCR molecules, preferably in a single chain format, can be used therapeutically, or in performing in vitro or in vivo assays as disclosed herein. Substantial purity can be determined by a variety of standard techniques such as chromatography and gel electrophoresis.

Truncated TCR molecules of the invention contain a TCR molecule that is sufficiently truncated so the TCR molecule of the invention can be secreted into culture medium after expression. Thus, a truncated TCR molecule, sc-TCR, TCR fusion or complex will typically not include regions rich in hydrophobic residues, typically the transmembrane and cytoplasmic domains of the TCR molecule. Thus, for example, for a preferred truncated TCR molecule of the invention, preferably from about amino acid residues 199 to 237 of the β chain and from about amino acid residues 193 to 230 of the α chain of the TCR molecule are not included in the truncated TCR complex.

By the term "soluble" or similar term is meant that a TCR molecule of the invention, usually but not exclusively a single chain construct, is not readily sedimented under low G-force centrifugation (e.g. less than about 30,000 revolutions per minute in a standard centrifuge) from an aqueous buffer, e.g., cell media. Further, the molecule is soluble if it remains in aqueous solution at a temperature greater than about 5-37° C. and at or near neutral pH in the presence of low or no concentration of an anionic or non-ionic detergent. Under these conditions, a soluble protein will often have a low sedimentation value, e.g., less than about 10 to 50 Svedberg units.

Aqueous solutions referenced herein typically have a buffering compound to establish pH, typically within a pH range of about 5-9, and an ionic strength range between about 2 mM and 500 mM. Sometimes a protease inhibitor or mild non-ionic detergent is added. Additionally, a carrier protein may be added if desired such as bovine serum albumin (BSA) or human serum albumin (HSA) to a few mg/ml. Exemplary aqueous buffers include standard phosphate buffered saline, Tris-buffered saline, or other well-known buffers and cell media formulations.

The present TCR molecules are suitable for in vitro or in vivo use with a variety of cells that are cancerous, pre-cancerous, or tumorigenic. Preferably, such cells express high levels of p53 protein when compared to normal (wild-type) cells that are not known to be cancerous, pre-cancerous, or tumorigenic.

Molecules of the invention will be especially useful to a human patient who has or is suspected of having a malignant disease, disorder or condition associated with abnormal expression of p53 (e.g., an at least two-fold overexpression of the molecule). For example, molecules of the invention or derivatives thereof will be particularly useful in targeting tumors in human patients associated with abnormal expression of p53. Specific examples of diseases which may be treated in accordance with the invention include cancers, e.g., breast, prostate, etc., well as other specific disorders or conditions mentioned herein.

Administration of molecules of the invention may be made by a variety of suitable routes including oral, topical (including transdermal, buccal or sublingal), nasal and parenteral (including intraperitoneal, subcutaneous, intravenous, intradermal or intramuscular injection) with oral or parenteral being generally preferred. It also will be appreciated that the preferred method of administration and dosage amount may vary with, for example, the condition and age of the recipient. Effective dosages may be monitored by determining standard clinical therapeutic endpoints such as tumor regression, decrease in expression of cancer—specific markers (including p53], decreased cell proliferation, improved or normal biopsy results, and the like.

Molecules of the invention may be used in therapy alone or in conjunction with other medicaments such as those with recognized pharmacological activity to treat the desired indications. Exemplary medicaments include recognized therapeutics such as surgery, radiation, chemotherapy and other forms of immunotherapy (e.g., vaccines, antibody-based therapies). The molecule of this invention can be administered before, during or after such therapies as needed.

While one or more molecules of the invention may be administered alone, they also may be present as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof. Pharmaceutical compositions of the invention in general comprise one or more TCR molecules of the invention or DNA constructs coding for such TCR molecules together with one or more acceptable carriers. The carriers must be "acceptable" in the sense of being compatible with other ingredients of the formulation and not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active molecules of the invention.

For parenteral application, particularly suitable are solutions, preferably oily or aqueous solutions as well as suspensions, emulsions, or implants, including suppositories. Ampoules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

Therapeutic compounds of the invention also may be incorporated into liposomes. The incorporation can be carried out according to known liposome preparation procedures, e.g. sonication and extrusion. Suitable conventional methods of liposome preparation are also disclosed in e.g. A. D. Bangham et. al., *J. Mol. Biol.*, 23:238-252 (1965); F. Olson et. al., *Biochim. Biophys. Acta*, 557:9-23 (1979); F. Szoka et. al., *Proc. Nat. Acad. Sci.*, 75:4194-4198 (1978); S. Kim et. al., *Biochim. Biophys. Acta*, 728:339-348 (1983); and Mayer et. al., *Biochim. Biophys. Acta*, 858:161-168 (1986).

The invention also provides methods for invoking an immune response in a mammal such as a human, including vaccinating a mammal such as a human against a targeted disorder associated with the overexpression of p53 such as cancer.

These methods comprise administering to a mammal an effective amount of a DNA sequence that comprises a DNA vector that codes for a TCR molecules of the invention. Preparation of expression vectors of TCR molecules is described above and in the Examples which follow. Methods for administration of plasmid DNA, uptake of that DNA by cells of the administered subject and expression of protein have been reported. See Ulmer, J. B., et. al., Science (1993) 259: 1745-1749.

DNA vectors that encode TCR molecules of the invention are suitably administered to a mammal including a human preferably by intramuscular injection. Administration of cDNA to skeletal muscle of a mammal with subsequent uptake of administered expression vector by the muscle cells and expression of protein encoded by the DNA has been described by Ulmer et. al. and represents an exemplary protocol [Ulmer, J. B., et. al., *Science* 259: 1745-1749]. The optimal dose for a given therapeutic application can be determined by conventional means.

In addition to treatment of human disorders, TCR molecules of the invention and DNA constructs of the invention that encode such TCR molecules will have significant use for veterinary applications, e.g., treatment of disorders of livestock such as cattle, sheep, etc. and pets such as dogs and cats using the cognate p53 antigens and MHC molecules appropriate for the animal species.

It will be appreciated that actual preferred amounts of a given TCR molecule of the invention or DNA construct coding for same used in a given therapy will vary according to the particular active compound or compounds being utilized, the particular compositions formulated, the mode of application, the particular site of administration, the patient's weight, general health, sex, etc., the particular indication being treated, etc. and other such factors that are recognized by those skilled in the art including the attendant physician or veterinarian. Optimal administration rates for a given protocol of administration can be readily determined by those skilled in the art using conventional dosage determination tests conducted e.g. with regard to the foregoing guidelines and the assays disclosed herein.

A "polypeptide" refers to any polymer preferably consisting essentially of any of the 20 natural amino acids regardless of its size. Although the term "protein" is often used in reference to relatively large proteins, and "peptide" is often used in reference to small polypeptides, use of these terms in the field often overlaps. The term "polypeptide" refers generally to proteins, polypeptides, and peptides unless otherwise noted. Peptides useful in accordance with the present invention in general will be generally between about 0.1 to 100 KD or greater up to about 1000 KD, preferably between about 0.1, 0.2, 0.5, 1, 2, 5, 10, 20, 30 and 50 KD as judged by standard molecule sizing techniques such as centrifugation or SDS-polyacrylamide gel electrophoresis.

As used herein, the term "cell" is intended to include any primary cell or immortalized cell line, any group of such cells as in, a tissue or an organ. Preferably the cells are of mammalian and particularly of human origin, and can be infected by one or more pathogens. A "host cell" in accord with the invention can be an infected cell or it can be a cell such as *E. coli* that can be used to propagate a nucleic acid described herein.

All documents mentioned herein are incorporated herein by reference. The following non-limiting examples are illustrative of the invention.

EXAMPLE 1

Construction of 264 Single-Chain (sc) TCR

The T cell clone, 264, recognizes a peptide fragment (aa 264-272; LLGRNSFEV) [SEQ ID NO. 1] of the human wild-type tumor suppresser protein p53 restricted by HLA-A2.1. The T cell receptor gene was cloned into a three-domain single-chain format previously shown to produce soluble TCR and functional receptor molecules.

In brief, mRNA was isolated from the T cell clone and cDNA was made using the Marathon cDNA Amplification Kit (Clontech). Sequencing of cDNA clones identified two distinct V alpha chains (V alpha 3 and V alpha 13) and a single V beta chain (V beta 3). The cDNA was used as a template in polymerase chain reaction (PCR) with primers KC228 and KC229 or KC226 and KC227 to produce 5' SfiI-3' SpeI V alpha 3 or V alpha 13 fragments respectively. The same DNA was then used as a PCR template with primers PRIB4 and KC176 to generate a 5' XhoI-3' XmaI V beta C beta chain fragment. The C beta chain was truncated just before the cysteine residue at amino acid 127 of the full length C beta chain.

The alpha and beta chain fragments were cloned into the pGEM-T Easy Vector System (Promega) for DNA sequence determination. Correct fragments were restriction digested and cloned into expression vector pKC60 (described previously in pending U.S. patent application Ser. No. 08/813,781) to create two V alpha-$(G_4S)_4$ (SEQ ID NO: 23) V beta C beta scTCR molecules, 264-A (with V alpha 3) and 264-B (with V alpha 13).

The DNA constructs described above (264-A and 264-B) were re-amplified by PCR with primers ET-TCRF1 and KC170 or ET-TCRF2 and KC170, respectively, to generate 5' AgeI-3' ClaI DNA fragments. The fragments were cloned into the pGEM-T Easy Vector System for DNA sequence determination.

The 5' AgeI-3' ClaI fragments were then used as the template DNA in PCR with primers KC232 and KC208 or KC231 and KC208, respectively, to produce 5' AgeI-3' HpaI DNA fragments for cloning to produce the CD3 zeta fusion molecule or vectors comprising such molecules (described below) and eventually the 264 IL2 fusion molecule or vectors comprising such molecules (described below).

EXAMPLE 2

Construction of the CD3 Zeta Fusion Shuttle Vector

To determine which of the two V alpha chains was functional, both the 264-A and 264-B sc-TCR were expressed as CD3 zeta fusion molecules.

Construction of a "shuttle vector" has been previously described in pending U.S. application Ser. No. 09/422,375, the disclosure of which is incorporated herein by reference.

Briefly, alpha and beta chain TCR fragments were cloned into the expression vector pKC60 to create a V alpha-$(G_4S)_4$ (SEQ ID NO: 23) V beta C beta scTCR molecule. The new vector was named pNAG2 (FIG. 9). pNAG2 was then re-amplified by PCR with primers KC203 and KC208 to generate a 5' AgeI-3' HpaI/BspEI/NruI/ClaI DNA fragment. The scTCR fragment was cloned into the pGEM-T Easy Vector System and this new pGEM-based vector was then used as a "shuttle vector" for introduction Sc-Fv DNA was then restriction digested and cloned into the "shuttle vector" downstream of the sc-TCR. To connect the sc-TCR and sc-Fv together as a single-chain fusion protein, the "shuttle vector" was digested with the appropriate restriction enzymes to drop out the previous linker DNA fragment and allow for ligation of linker sequences between the sc-TCR and the sc-Fv.

In the "shuttle vector" design outlined above, a stop codon and splice site were introduced between the NruI and ClaI restriction sites as part of the PCR amplification of the scTCR with "back" primer KC208. To aid in downstream purification of the bispecific sc protein, a set of annealed oligonucleotides (KC237 and KC238) was designed to introduce a 3' EE tag (EEEEYMPME) (SEQ ID NO.6] with a stop codon and splice site. The annealed oligonucleotide pair was cloned 5'NruI-3'ClaI into the "shuttle vector" already encoding for the complete bispecific sc-TCR molecule.

After cloning the scTCR, sc-Fv, linker, and tag DNA fragments into the "shuttle vector" to complete the bispecific sc molecule design, the DNA was restriction digested (AgeI-ClaI) and cloned into the mammalian cell expression vector pSUN27 (FIG. 2) (previously described in the pending U.S. application Ser. No. 08/943,086 to create pBISP/149 and pBISP/D011.10 (FIG. 3). pBISP/D011.10 can be generated by one skilled in the art using pBISP/149 which is deposited as pSUN28 and any of three D011.10scTCR plasmids (pSUN18—ATCC#97895, pSUN19—ATCC#97896, or pSUN27-ATCC#209276). The disclosure of the U.S. Ser. No. 08/943, 086 is incorporated herein by reference.

Construction of the CD3 Zeta Fusion Vector

In brief, murine cDNA was used as the template in polymerase chain reaction (PCR) with primers KC312 and KC304 to produce a 5'HpaI-3'ClaI murine CD3 zeta fragment.

The murine CD3 zeta fragment was cloned into the pGEM-T Easy Vector System for DNA sequence determination. The correct fragment was restriction digested and cloned into the "shuttle vector", effectively removing the existing linker, sc-FV, and EE tag.

After cloning the CD3 zeta gene into the "shuttle vector", the DNA was digested AgeI-HpaI to allow for ligation with the 264-A and 264-B sc-TCR fragments (described above), creating two new sc-TCR/CD3 zeta fusions. Lastly, the new DNA preparations were restriction digested (AgeI-ClaI) and cloned into the mammalian cell expression vector pSUN28 (pBISP/D011.10 vector), FIG. 3 previously described in pending U.S. patent application Ser. No. 09/422,375.

EXAMPLE 3

Expression of 264 scTCR/CD3 Zeta Fusion Molecules

Jurkat cells were prepared for transfection by washing with cold DPBS. The cells were resuspended in DPBS and mixed with 20 µg of PvuI linearized 264-A/CD3 zeta or 264-B/CD3 zeta DNA. After five minutes on ice, the cells were electroporated using a Gene Pulser (BioRad) set to deliver one pulse of 250 volts, 960 µFd. The pulsed cells were placed on ice for five minutes. The cells were diluted into 10 ml of 10% IMDM medium (IMDM, 10% FBS, 2 mM glutamine) and grown in a T-25 cm$^2$ TC flask overnight at 37° C. with 5% $CO_2$ The next day, the cells were plated in 96 well plates with selective medium (10% IMDM plus 1.0 mg/ml G418). After 1 week, the concentration of G418 was increased to 2 mg/ml. The growing colonies were re-fed approximately two weeks after transfection and screened about one week later.

The transfected Jurkat cells were screened for surface expression of scTCR using flow cytometry analysis. Positive transfectants were identified by staining with a fluorescent-tagged mAb (H57-597) which detects a portion of the C beta domain of murine TCR.

EXAMPLE 4

Identificaton of the Correct 264 scTCR V Alpha Domain

Transfected Jurkat cells which expressed either the 264-A or 264-B version of the CD3 zeta fusion molecule were used in a cell activation assay. In the assay, the HLA-A2 presenting cell line T2 was used as the APC. The T2 cells were loaded with 264 peptide (or irrelevant peptide) overnight at 37° C. with 5% $CO_2$. The following day, the transfected Jurkat lines were added and allowed to interact with the peptide-pulsed APCs overnight.

Specific stimulation of the transfectants by 264-loaded APCs was assessed using an IL-2 ELISA. An anti-human IL-2 mAb was coated passively overnight on a 96 well plate. The plate was washed and blocked with 10% FBS/DPBS for 1 hour. The blocking reagent was flicked out and supernatants from the assay were added to the plate for 1 hour at 37° C. After washing, the bound IL-2 was detected using another anti-IL-2 mAb conjugated to biotin. Following 45 minutes at 37° C., the plate was washed and streptavidin-HRP was added for 15 minutes. Finally, the plate was washed and developed using ABTS substrate. Absorbance was read at 405 nm.

Based on the cell activation assay, the V alpha 3 domain is functional. Only cells expressing the 264-A molecule were stimulated to produce IL-2 in the presence of 264 peptide-loaded APCs.

Table 1, shown on the following page, shows the primary sequence of various oligonucleotides used in the forgoing examples.

TABLE 1

| | | |
|---|---|---|
| KC228 | SEQ ID NO. 7 | 5'-gag gtg gcc cag ccg gcc atg gcc cag tca gtg acg cag c-3' |
| KC229 | SEQ ID NO. 8 | 5'-gag gtg act agt gtc tgg ctt tat aat tag-3' |
| KC226 | SEQ ID NO. 9 | 5'-gag gtg gcc cag ccg gcc atg gcc gag cag gtg gag cag c-3' |
| KC227 | SEQ ID NO. 10 | 5'-gag gtg act agt gtt tga ttt aac aga gag-3' |
| PRIB4 | SEQ ID NO. 11 | 5'-ggg ggg ctc gag caa ttc aaa agt cat tca gac tc-3' |
| KC176 | SEQ ID NO. 12 | 5'-gag gtg gag ccc ggg gtc tgc tcg gcc cca ggc-3' |
| ET-TORF1 | SEQ ID NO. 13 | 5'-ccc acc ggt cag tca gtg acg cag ccc-3' |
| KC170 | SEQ ID NO. 14 | 5'-gtg gag ttc gaa aag tgt act tac gtt tgt ctg ctc ggc ccc ag-3' |
| ET-TCRF2 | SEQ ID NO. 15 | 5'-ccc acc ggt gag cag gtg gag cag ctt-3' |
| KC232 | SEQ ID NO. 16 | 5'-gag gtg acc ggt cag tca gtg acg cag c-3' |
| KC208 | SEQ ID NO. 17 | 5'-gtg gag atc gat aag tgt act tac gtt ttc att atc gcg atc cgg agt taa cgt ctg ctc ggc ccc ag-3' |
| KC231 | SEQ ID NO. 18 | 5'-gag gtg acc ggt gag cag gtg gag cag c-3' |
| KC312 | SEQ ID NO. 19 | 5'-gag gtg gtt aac gat ccc aaa ctc tgc tac ttg cta gat gga atc etc-3' |
| KC304 | SEQ ID NO. 20 | 5'-gag gtg atc gat aag tgt act tac gtt ttt agc gag ggg gca ggg c-3' |

Although a preferred embodiment of the invention has been described using specific terms, such description is for illustrative purposes only, and it is to be understood that changes and variations may be made without departing from the spirit or scope of the following claims.

What is claimed is:

1. An isolated T cell receptor (TCR) comprising a Vα3 chain as set forth as residues 1-113 of SEQ ID NO. 2 and a Vβ3 chain as set forth as residues 138-251 of SEQ ID NO. 2, wherein the TCR is capable of binding a p53 peptide comprising the sequence set forth as Leu Leu Gly Arg Asn Ser Phe Glu Val (SEQ ID NO. 1) in the context of an MHC molecule, wherein the MHC molecule comprises an HLA A2 molecule.

2. The isolated TCR of claim 1, wherein the Vα-chain comprises covalently linked in sequence: a) a Vα chain and b) a Cα chain.

3. The isolated TCR of claim 1, wherein the Vβ-chain comprises covalently linked in sequence: a Vβ chain, and a Cβ sequence.

4. The isolated TCR of claim 1, wherein binding is determined by monitoring binding of the TCR to an MHC molecule complexed with a peptide comprising the amino acid sequence according to SEQ ID NO:1, wherein the MHC molecule comprises an HLA A2 molecule.

5. The isolated TCR of claim 4, wherein the binding is monitored in a TCR ELISA or a standard TCR binding assay.

6. The isolated TCR of claim 4, wherein binding is monitored by measuring signal transduction by the TCR.

7. The isolated TCR of claim 4, wherein binding between the amino acid sequence and the TCR molecule is increased by at least about 2 fold when compared to a control TCR heterodimer.

8. The isolated TCR of claim 1, further comprising a Cβ sequence as set forth as residues 252-377 of SEQ ID NO:2.

9. The isolated TCR of claim 1, further comprising a Cα sequence as set forth as SEQ ID NO:3.

10. The isolated TCR of claim 1, wherein said TCR comprises a heterodimer.

11. The isolated TCR of claim 1, wherein said TCR comprises a single chain TCR (scTCR).

12. The isolated single chain TCR (scTCR) of claim 11, wherein the Vα3 chain is covalently linked to a Vβ3 chain by a peptide linker sequence.

13. The scTCR of claim 11, wherein the scTCR comprises a transmembrane domain.

14. The scTCR of claim 11, wherein the scTCR comprises a CD zeta cytoplasmic signaling domain.

15. A single chain T-cell receptor (scTCR), wherein the scTCR comprises in sequence a) a Vα3 chain as set forth as amino acid residues 1-113 of SEQ ID NO:2, b) a peptide linker, and c) a Vβ3 chain as set forth as amino acid residues 138-251 of SEQ ID NO. 2.

16. The scTCR of claim 15 further comprising a Cβ chain as set forth as amino acid residues 252-377 of SEQ ID NO. 2 linked to the C-terminus of the Vβ3 chain.

17. The scTCR of any of claims 15-16, further comprising a fragment of the Cα chain as provided in FIG. 5 (SEQ ID NO: 3), the fragment being covalently linked between the C-terminus of the Vα chain and the N-terminus of the peptide linker.

18. The scTCR of claim 15, wherein the peptide linker has the following sequence: Gly Gly Gly Gly Ser (SEQ ID NO: 5) repeated at least four times.

19. An isolated T cell receptor comprising SEQ ID NO:2.

20. The isolated T cell receptor of claim 19, further comprising the Cα chain as set forth as SEQ ID NO:3.

21. An isolated T cell receptor consisting of SEQ ID NO:2, 3, and 5.

22. The scTCR of claim 15, wherein the Vα3 chain consists of the amino acid sequence as set forth as residues 1-113 of SEQ ID NO: 2 and the Vβ3 chain consists of the amino acid sequence as set forth as residues 138-251 of SEQ ID NO: 2.

23. The TCR of claim 1, wherein the Vα3 chain consists of the amino acid sequence as set forth as residues 1-113 of SEQ ID NO:2 and wherein the Vβ3 chain consists of the amino acid sequence as set forth as residues 138-251 of SEQ ID NO: 2.

* * * * *